US012752118B2

(12) United States Patent
Babakhani

(10) Patent No.: US 12,752,118 B2
(45) Date of Patent: Oct. 6, 2026

(54) CLOSED-LOOP WIRELESS STIMULATION SYSTEMS WITH WIRELESSLY POWERED STIMULATORS AND RECORDERS

(71) Applicant: The Regents of the University of California, Oakland, CA (US)

(72) Inventor: Aydin Babakhani, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 245 days.

(21) Appl. No.: 18/549,313

(22) PCT Filed: Mar. 10, 2022

(86) PCT No.: PCT/US2022/071066
§ 371 (c)(1),
(2) Date: Sep. 6, 2023

(87) PCT Pub. No.: WO2022/192894
PCT Pub. Date: Sep. 15, 2022

(65) Prior Publication Data

US 2024/0173551 A1 May 30, 2024

Related U.S. Application Data

(60) Provisional application No. 63/159,219, filed on Mar. 10, 2021.

(51) Int. Cl.
*A61N 1/36* (2006.01)
*A61N 1/02* (2006.01)
(Continued)

(52) U.S. Cl.
CPC ......... *A61N 1/36139* (2013.01); *A61N 1/025* (2013.01); *A61N 1/37235* (2013.01);
(Continued)

(58) Field of Classification Search
CPC ................ A61N 1/36139; A61N 1/025; A61N 1/37288; A61N 1/3787; A61N 1/36062; A61N 1/37211; A61B 5/4836
See application file for complete search history.

(56) References Cited

U.S. PATENT DOCUMENTS 3,945,387 A 3/1976 Adams
4,220,156 A 9/1980 Morgan et al.
(Continued)

FOREIGN PATENT DOCUMENTS

AU 2018217270 A1 8/2018
CN 104767291 A 7/2015
(Continued)

OTHER PUBLICATIONS

Extended European Search Report for European Application No. 21908064.5, Search completed Nov. 29, 2024, Mailed Dec. 9, 2024, 13 Pgs.

(Continued)

*Primary Examiner* — Paula J Stice
(74) *Attorney, Agent, or Firm* — KPPB LLP

(57) ABSTRACT

Systems and methods for wirelessly powered biomedical treatment systems with closed-loop wireless implantable treatment devices for recording and stimulation are described. In an embodiment, a treatment system, includes: at least one implantable treatment device implantable in a location with respect to a body part, where the at least one implantable treatment device includes: an energy harvesting circuit configured to harvest ambient energy, a sensing circuit configured to sense bioelectrical signals, an stimulator circuit coupled to a set of electrodes to deliver energy, and a communication circuit configured to control the stimulation delivery circuit to deliver energy via at least one
(Continued)

electrode from the set of electrodes in response to wireless control signals received from an external controller.

24 Claims, 14 Drawing Sheets

(51) Int. Cl.
*A61N 1/372* (2006.01)
*A61N 1/378* (2006.01)

(52) U.S. Cl.
CPC ..... *A61N 1/37252* (2013.01); *A61N 1/37288* (2013.01); *A61N 1/3787* (2013.01)

(56) References Cited

U.S. PATENT DOCUMENTS

| | | | |
|---|---|---|---|
| 4,301,401 | A | 11/1981 | Roof et al. |
| 4,388,927 | A | 6/1983 | Schober |
| 4,459,989 | A | 7/1984 | Borkan |
| 4,532,930 | A | 8/1985 | Crosby et al. |
| 4,612,940 | A | 9/1986 | Kasevich et al. |
| 4,719,919 | A | 1/1988 | Marchosky et al. |
| 5,157,340 | A | 10/1992 | Walton et al. |
| 5,464,429 | A | 11/1995 | Hedberg et al. |
| 5,497,099 | A | 3/1996 | Walton |
| 5,522,865 | A | 6/1996 | Schulman et al. |
| 5,534,947 | A | 7/1996 | Saionji |
| 5,630,426 | A | 5/1997 | Eggers et al. |
| 5,749,909 | A | 5/1998 | Schroeppel et al. |
| 6,073,050 | A | 6/2000 | Griffith |
| 6,402,689 | B1 | 6/2002 | Scarantino et al. |
| 6,423,056 | B1 | 7/2002 | Ishikawa et al. |
| 6,735,472 | B2 | 5/2004 | Helland |
| 6,813,518 | B2 | 11/2004 | Kuepper |
| 6,870,503 | B2 | 3/2005 | Mohamadi |
| 6,882,315 | B2 | 4/2005 | Richley et al. |
| 7,010,340 | B2 | 3/2006 | Scarantino et al. |
| 7,043,301 | B1 | 5/2006 | Kroll et al. |
| 7,132,173 | B2 | 11/2006 | Daulton |
| 7,177,341 | B2 | 2/2007 | Mccorkle |
| 7,180,421 | B2 | 2/2007 | Pahlavan et al. |
| 7,228,228 | B2 | 6/2007 | Bartlett et al. |
| 7,339,883 | B2 | 3/2008 | Santhoff et al. |
| 7,483,735 | B2 | 1/2009 | Liu et al. |
| 7,610,092 | B2 | 10/2009 | Cowan et al. |
| 7,751,881 | B2 | 7/2010 | Cowan et al. |
| 7,972,117 | B1 | 7/2011 | Macdonald |
| 8,032,227 | B2 | 10/2011 | Parramon et al. |
| 8,126,418 | B2 | 2/2012 | Nowak et al. |
| 8,188,841 | B2 | 5/2012 | Dowla et al. |
| 8,290,600 | B2 | 10/2012 | Hastings et al. |
| 8,547,248 | B2 | 10/2013 | Zdeblick et al. |
| 8,552,597 | B2 | 10/2013 | Song et al. |
| 8,634,919 | B1 | 1/2014 | Hou et al. |
| 8,644,933 | B2 | 2/2014 | Ozawa et al. |
| 8,670,824 | B2 | 3/2014 | Anderson et al. |
| 8,939,928 | B2 | 1/2015 | Savoie et al. |
| 9,026,212 | B2 | 5/2015 | Imran |
| 9,031,658 | B2 | 5/2015 | Chiao et al. |
| 9,037,223 | B2 | 5/2015 | Oral et al. |
| 9,153,642 | B2 | 10/2015 | Li et al. |
| 9,161,693 | B2 | 10/2015 | Rizwan |
| 9,168,380 | B1 | 10/2015 | Greenhut et al. |
| 9,168,383 | B2 | 10/2015 | Jacobson et al. |
| 9,205,258 | B2 | 12/2015 | Simon et al. |
| 9,270,137 | B2 | 2/2016 | Greene |
| 9,277,874 | B2 | 3/2016 | Joshi et al. |
| 9,421,369 | B2 | 8/2016 | Liu et al. |
| 9,423,438 | B2 | 8/2016 | Lin et al. |
| 9,425,863 | B2 | 8/2016 | Kim et al. |
| 9,486,621 | B2 | 11/2016 | Howard et al. |
| 9,522,270 | B2 | 12/2016 | Perryman et al. |
| 9,544,068 | B2 | 1/2017 | Arbabian et al. |
| 9,669,223 | B2 | 6/2017 | Auricchio et al. |
| 9,669,230 | B2 | 6/2017 | Koop |
| 9,685,793 | B2 | 6/2017 | Zargham et al. |
| 9,700,712 | B2 | 7/2017 | Towe |
| 9,711,978 | B2 | 7/2017 | Manova-elssibony et al. |
| 9,825,361 | B2 | 11/2017 | Pachler et al. |
| 9,953,195 | B2 | 4/2018 | Turner et al. |
| 10,014,730 | B2 | 7/2018 | Nayak |
| 10,238,872 | B2 | 3/2019 | Pivonka et al. |
| 10,312,743 | B2 | 6/2019 | Ouda et al. |
| 10,369,369 | B2 | 8/2019 | Perryman et al. |
| 10,493,288 | B2 | 12/2019 | Hastings et al. |
| 10,530,421 | B2 | 1/2020 | Muthali et al. |
| 10,537,403 | B2 | 1/2020 | Vora et al. |
| 10,646,164 | B1 | 5/2020 | Perryman et al. |
| 10,742,222 | B2 | 8/2020 | Emira et al. |
| 10,742,261 | B2 | 8/2020 | Nabki et al. |
| 10,978,917 | B2 | 4/2021 | Freitas et al. |
| 11,016,051 | B1 | 5/2021 | Sinko et al. |
| 11,048,893 | B2 | 6/2021 | Babakhani et al. |
| 11,050,263 | B2 | 6/2021 | Bae et al. |
| 11,071,857 | B2 | 7/2021 | Sun et al. |
| 11,106,230 | B2 | 8/2021 | Karunasiri et al. |
| 11,515,733 | B2 | 11/2022 | Babakhani et al. |
| 11,541,238 | B2 | 1/2023 | Andresen et al. |
| 11,712,559 | B2 | 8/2023 | Sun et al. |
| 11,911,625 | B2 | 2/2024 | Babakhani et al. |
| 12,052,533 | B2 | 7/2024 | Lyu et al. |
| 12,062,926 | B2 | 8/2024 | Babakhani et al. |
| 12,320,769 | B2 | 6/2025 | Babakhani et al. |
| 2002/0064245 | A1 | 5/2002 | McCorkle |
| 2002/0103507 | A1 | 8/2002 | Helland |
| 2002/0137991 | A1 | 9/2002 | Scarantino et al. |
| 2003/0032986 | A1 | 2/2003 | Kupper |
| 2004/0054471 | A1 | 3/2004 | Bartlett et al. |
| 2004/0058186 | A1 | 3/2004 | Daulton |
| 2004/0095287 | A1 | 5/2004 | Mohamadi |
| 2004/0108954 | A1 | 6/2004 | Richley et al. |
| 2005/0058121 | A1 | 3/2005 | Santhoff et al. |
| 2005/0256549 | A1 | 11/2005 | Holzer |
| 2006/0085039 | A1 | 4/2006 | Hastings et al. |
| 2006/0126577 | A1 | 6/2006 | Yano et al. |
| 2006/0136004 | A1 | 6/2006 | Cowan et al. |
| 2007/0067004 | A1 | 3/2007 | Boveja et al. |
| 2007/0085719 | A1 | 4/2007 | Maxim et al. |
| 2007/0118187 | A1 | 5/2007 | Denker et al. |
| 2007/0120677 | A1 | 5/2007 | Park et al. |
| 2007/0173214 | A1 | 7/2007 | Mickle et al. |
| 2007/0211786 | A1 | 9/2007 | Shattil |
| 2007/0225781 | A1 | 9/2007 | Saadat et al. |
| 2007/0293895 | A1 | 12/2007 | Cowan et al. |
| 2008/0021505 | A1 | 1/2008 | Hastings et al. |
| 2008/0039904 | A1 | 2/2008 | Bulkes et al. |
| 2008/0114417 | A1 | 5/2008 | Leyde |
| 2008/0252422 | A1 | 10/2008 | Dowla et al. |
| 2008/0262580 | A1 | 10/2008 | Gerber et al. |
| 2008/0269833 | A1 | 10/2008 | Scott et al. |
| 2008/0288039 | A1 | 11/2008 | Reddy |
| 2008/0300660 | A1 | 12/2008 | John |
| 2008/0306359 | A1 | 12/2008 | Zdeblick et al. |
| 2009/0157141 | A1 | 6/2009 | Chiao et al. |
| 2009/0219139 | A1 | 9/2009 | Slesinski |
| 2009/0292341 | A1 | 11/2009 | Parramon et al. |
| 2010/0076517 | A1 | 3/2010 | Imran |
| 2010/0114189 | A1 | 5/2010 | Donofrio et al. |
| 2010/0114243 | A1 | 5/2010 | Nowak et al. |
| 2010/0308974 | A1 | 12/2010 | Rowland et al. |
| 2011/0022025 | A1 | 1/2011 | Savoie et al. |
| 2011/0144851 | A1 | 6/2011 | Gremminger et al. |
| 2011/0169607 | A1 | 7/2011 | Paulson |
| 2011/0288615 | A1 | 11/2011 | Armstrong et al. |
| 2012/0008714 | A1 | 1/2012 | Rizwan |
| 2012/0071203 | A1 | 3/2012 | Wong |
| 2012/0095531 | A1 | 4/2012 | Derbas et al. |
| 2012/0109236 | A1 | 5/2012 | Jacobson et al. |
| 2012/0161787 | A1 | 6/2012 | Potyrailo et al. |
| 2012/0166095 | A1 | 6/2012 | Potyrailo et al. |
| 2012/0183097 | A1 | 7/2012 | Ishizaki |
| 2012/0197566 | A1 | 8/2012 | Habic et al. |
| 2012/0239118 | A1 | 9/2012 | Ozawa et al. |

(56) References Cited

U.S. PATENT DOCUMENTS

2012/0256492 A1 10/2012 Song et al.
2013/0066400 A1 3/2013 Perryman et al.
2013/0109987 A1 5/2013 Kunis et al.
2013/0123882 A1 5/2013 Towe
2013/0154611 A1 6/2013 Pate et al.
2013/0197380 A1 8/2013 Oral et al.
2013/0211477 A1 8/2013 Cullen et al.
2013/0238057 A1 9/2013 Goto
2014/0011286 A1 1/2014 Potyrailo et al.
2014/0011543 A1 1/2014 Li et al.
2014/0046389 A1 2/2014 Anderson et al.
2014/0058239 A1 2/2014 Joshi et al.
2014/0062666 A1 3/2014 Patterson
2014/0094674 A1 4/2014 Nurmikko et al.
2014/0140364 A1 5/2014 Charles et al.
2014/0198062 A1 7/2014 Kreutzer et al.
2014/0243848 A1 8/2014 Auricchio et al.
2014/0252543 A1 9/2014 Li et al.
2014/0309947 A1 10/2014 Gryska et al.
2014/0336474 A1 11/2014 Arbabian et al.
2014/0375261 A1 12/2014 Manova-Elssibony et al.
2015/0042358 A1 2/2015 Lin et al.
2015/0057557 A1 2/2015 Howie et al.
2015/0076920 A1 3/2015 Zargham et al.
2015/0088115 A1 3/2015 Smith
2015/0127068 A1 5/2015 Simon et al.
2015/0130293 A1 5/2015 Hajimiri et al.
2015/0157868 A1 6/2015 Franke et al.
2015/0217123 A1 8/2015 Deterre et al.
2015/0229139 A1 8/2015 Greene
2015/0297900 A1 10/2015 Perryman et al.
2015/0343205 A1 12/2015 Howard et al.
2015/0356332 A1 12/2015 Turner et al.
2016/0008602 A1 1/2016 Perryman et al.
2016/0038739 A1 2/2016 Liu et al.
2016/0048710 A1 2/2016 Nekoogar et al.
2016/0144171 A1 5/2016 Zhu
2016/0149441 A1 5/2016 Nayak
2016/0204765 A1 7/2016 Ferriss et al.
2016/0228718 A1 8/2016 Koop
2016/0267769 A1 9/2016 Rokhsaz et al.
2016/0317060 A1 11/2016 Connor
2016/0338798 A1 11/2016 Vora et al.
2016/0380754 A1 12/2016 Chen et al.
2017/0001003 A1 1/2017 Pivonka et al.
2017/0066334 A1 3/2017 Sindia et al.
2017/0069967 A1 3/2017 Shrekenhamer
2017/0164878 A1 6/2017 Connor
2017/0195072 A1 7/2017 Lomnitz
2017/0234818 A1 8/2017 Jesme et al.
2017/0303505 A1 10/2017 Karsijns et al.
2018/0006730 A1 1/2018 Kuo et al.
2018/0069486 A1 3/2018 Ouda et al.
2018/0071539 A1 3/2018 Hastings et al.
2018/0123639 A1 5/2018 Muthali et al.
2018/0140831 A1 5/2018 Feldman et al.
2018/0143061 A1 5/2018 Strong
2018/0177431 A1 6/2018 Rottenberg
2018/0185657 A1 7/2018 Lebaron et al.
2018/0191199 A1 7/2018 Kim et al.
2018/0235692 A1 8/2018 Efimov et al.
2018/0256030 A1 9/2018 Lee et al.
2018/0283913 A1 10/2018 Chen et al.
2018/0303391 A1 10/2018 Roblyer et al.
2018/0333587 A1 11/2018 Howard
2018/0337534 A1 11/2018 Bell et al.
2019/0001139 A1 1/2019 Mishra et al.
2019/0097323 A1 3/2019 Rokhsaz et al.
2019/0097430 A1 3/2019 Bae et al.
2019/0143097 A1 5/2019 John et al.
2019/0180065 A1 6/2019 Babakhani et al.
2019/0209848 A1* 7/2019 Jenison .............. A61N 1/36125
2019/0224476 A1 7/2019 Sun et al.
2019/0238631 A1 8/2019 Aoyama et al.
2019/0247050 A1 8/2019 Goldsmith
2019/0247664 A1 8/2019 Irazoqui et al.
2019/0262605 A1 8/2019 Babakhani et al.
2019/0275328 A1 9/2019 Zitnik et al.
2019/0275331 A1* 9/2019 Zhu .................... A61N 1/36192
2019/0326785 A1 10/2019 Freitas et al.
2019/0366094 A1* 12/2019 Esteller .................... A61B 5/24
2019/0374777 A1 12/2019 Burdick et al.
2019/0388692 A1* 12/2019 Dinsmoor .......... A61N 1/36153
2020/0022607 A1 1/2020 Pratt et al.
2020/0046980 A1* 2/2020 Moffitt ................... G16H 20/40
2020/0106305 A1 4/2020 Calhoun et al.
2020/0155828 A1 5/2020 Shepard et al.
2020/0169118 A1 5/2020 Jung et al.
2020/0188675 A1* 6/2020 Marceglia .......... A61N 1/36135
2020/0195256 A1 6/2020 Emira et al.
2020/0376272 A1* 12/2020 Block ................ A61N 1/36071
2020/0391021 A1 12/2020 Sachs et al.
2021/0008373 A1* 1/2021 Single .................. A61N 1/0551
2021/0023373 A1 1/2021 Deshazo et al.
2021/0099015 A1 4/2021 Pivonka et al.
2021/0099196 A1 4/2021 Tang et al.
2021/0143678 A1 5/2021 Georgakopoulos
2021/0339017 A1 11/2021 Sun et al.
2021/0356417 A1 11/2021 Babakhani et al.
2021/0397257 A1 12/2021 Rogers et al.
2022/0008736 A1 1/2022 Babakhani et al.
2022/0095992 A1 3/2022 Guvenc et al.
2022/0103264 A1 3/2022 Babakhani et al.
2022/0158497 A1 5/2022 Babakhani et al.
2022/0252506 A1 8/2022 Babakhani et al.
2022/0264196 A1 8/2022 Lyu et al.
2022/0273944 A1 9/2022 Werneth et al.
2022/0379124 A1 12/2022 Babakhani et al.
2023/0028864 A1 1/2023 Fan et al.
2023/0081364 A1 3/2023 Babakhani et al.
2023/0181910 A1 6/2023 Werneth
2023/0319562 A1 10/2023 Lee et al.
2024/0115183 A1 4/2024 Rahmani et al.
2024/0146115 A1 5/2024 Babakhani et al.
2024/0178568 A1 5/2024 Rokhsaz et al.
2024/0238603 A1 7/2024 Babakhani et al.
2025/0317009 A1 10/2025 Babakhani et al.
2025/0341488 A1 11/2025 Babakhani et al.

FOREIGN PATENT DOCUMENTS

CN 103278203 B 8/2015
CN 113228464 A 8/2021
EP 3116385 B1 11/2019
EP 3884562 A1 9/2021
EP 4032165 A1 7/2022
EP 4110165 A1 1/2023
EP 4262972 A1 10/2023
JP 2002505930 A 2/2002
JP 2008516741 A 5/2008
JP 2008539004 A 11/2008
JP 2010527267 A 8/2010
JP 2014528800 A 10/2014
JP 2019510463 A 4/2019
JP 2019130360 A 8/2019
JP 2022507813 A 1/2022
JP 2022549118 A 11/2022
JP 2023515580 A 4/2023
WO 1996027327 A1 9/1996
WO 2000038783 A1 7/2000
WO 2007028035 A2 3/2007
WO 2007109656 A2 9/2007
WO 2011030804 A1 3/2011
WO 2012013201 A1 2/2012
WO 2013058958 A1 4/2013
WO 2016199142 A1 12/2016
WO 2017059540 A1 4/2017
WO 2017066121 A1 4/2017
WO 2017070322 A1 4/2017
WO 2017205565 A1 11/2017
WO 2018039162 A2 3/2018
WO 2018053467 A1 3/2018
WO 2018209437 A1 11/2018
WO 2020106440 A1 5/2020

(56) References Cited

FOREIGN PATENT DOCUMENTS

| | | | |
|---|---|---|---|
| WO | 2020106862 | A1 | 5/2020 |
| WO | 2020125839 | A1 | 6/2020 |
| WO | 2020106440 | A8 | 7/2020 |
| WO | 2020160026 | A1 | 8/2020 |
| WO | 2021005146 | A1 | 1/2021 |
| WO | 2021007071 | A1 | 1/2021 |
| WO | 2021007210 | A1 | 1/2021 |
| WO | 2021046313 | A1 | 3/2021 |
| WO | 2021055146 | A1 | 3/2021 |
| WO | 2021174215 | A1 | 9/2021 |
| WO | 2021183487 | A1 | 9/2021 |
| WO | 2021247490 | A1 | 12/2021 |
| WO | 2022133501 | A1 | 6/2022 |
| WO | 2021174215 | A9 | 9/2022 |
| WO | 2022192894 | A1 | 9/2022 |
| WO | 2023060090 | A1 | 4/2023 |
| WO | 2023108176 | A1 | 6/2023 |
| WO | 2024054854 | A2 | 3/2024 |
| WO | 2024054854 | A3 | 5/2024 |

OTHER PUBLICATIONS

Ahmadi et al., "A Class-E Power Amplifier With Wideband FSK Modulation for Inductive Power and Data Transmission to Medical Implants", IEEE Sensors Journal, IEEE, USA, Sep. 1, 2018, vol. 18, No. 17, pp. 7242-7252, XP011688526, ISSN: 1530-437X, DOI: 0.1109/JSEN.2018.2851605.

Ghovanloo et al., "A Wireless Implantable Multichannel Microstimulating System-on-a-Chip With Modular Architecture", IEEE Transactions on Neural Systems and Rehabilitation Engineering IEEE, USA, Sep. 1, 2007, vol. 15, No. 3, pp. 449-457, XP011348056, ISSN: 1534-4320, DOI: 10.1109/TNSRE.2007.903970.

Kim et al., "Integrated Wireless Neural Interface Based on the Utah Electrode Array", Biomedical Microdevices, Kluwer Academic Publishers, BO, Dec. 10, 2008, vol. 11, No. 2, pp. 453-466, XP019670986, ISSN: 1572-8781.

Muller et al., "A Minimally Invasive 64-Channel Wireless μECoG Implant", IEEE Journal of Solid-State Circuits, Jan. 1, 2015 , vol. 50, No. 1, pp. 344-359, XP011568753, ISSN: 0018-9200, DOI: 10.1109/JSSC.2014.2364824.

Piedade et al., "Visual Neuroprosthesis: a Non Invasive System for Stimulating the Cortex", IEEE transactions on Circuits and Systems Part I: Regular Papers, Dec. 1, 2005, pp. 2648-2662, XP055886580, ISSN: 1057-7122, DOI: 10.1109/TCSI.2005.857923.

Song et al., "A Brain Implantable Microsystem with Hybrid RF/IR Telemetry for Advanced Neuroengineering Applications", 2009 Annual International Conference of the Ieee Engineering in Medicine and Biology Society, Aug. 1, 2007, pp. 445-448, XP055135982, ISSN: 1557-170X, DOI: 10.1109/IEMBS.2007.4352319.

Sutardja et al., "Isolator-Less Near-Field RFID Reader for Sub-Cranial Powering/Data Link of Millimeter-Sized Implants", IEEE Journal of Solid-State Circuits, IEEE, USA, Jul. 1, 2018, vol. 53, No. 7, pp. 2032-2042, XP011685915, ISSN: 0018-9200, DOI: 10.1109/JSSC.2018.2822673.

Wong et al., "Cmos Stimulating Chips Capable of Wirelessly Driving 473 Electrodes for a Cortical Vision Prosthesis", Journal of Neural Engineering, Institute of Physics Publishing, Bristol, GB, Feb. 19, 2019, vol. 16, No. 2, p. 26025, XP020339940, ISSN: 1741-2552, DOI: 10.1088/1741-2552/AB021B.

Yang et al., "Challenges in Scaling Down of Free-Floating Implantable Neural Interfaces to Millimeter Scale", IEEE Access, IEEE, USA, Jul. 6, 2020, vol. 8, pp. 133295-133320, XP011801127, DOI: 10.1109/Access.2020.3007517.

Rahmani et al., "A Wireless Power Receiver with an On-chip Antenna for Millimeter-size Biomedical Implants in 180 nm SOI CMOS", IEEE MTT-S International Microwave symposium (IMS), Jun. 2017, pp. 300-303.

Rahmani et al., "An Integrated Battery-Less Wirelessly Powered RFID Tag with Clock Recovery and Data Transmitter for UWB Localization", Microwave, MTT-S International Symposium, Aug. 4-6, 2020, Los Angeles, CA, USA, pp. 460-463, doi: 10.1109/IMS30576.2020.9223821.

Rahmat-Samii et al., "Implanted antennas in medical wireless communications", Synthesis Lectures on Antennas, vol. 1, No. 1, 2005, pp. 1-82, doi: 10.2200/s00024ed1v01y200605ant001.

Rajavi et al., "An energy harvested ultra-low power transceiver for Internet of Medical Things", European Conference on Solid-State Circuits (ESSCIRC): 42nd Solid-State Circuits Conference, Lausanne, Switzerland, Sep. 12-15, 2016, pp. 133-136, doi: 10.1109/esscirc.2016.7598260.

Rajavi et al., "An RF-powered FDD Radio for Neural Microimplants", IEEE Journal of Solid-State Circuits, vol. 52, No. 5, May 1, 2017, pp. 1221-1229, XP011646410, ISSN: 0018-9200, doi: 10.1109/JSSC.2016.2645601.

Ramrakhyani et al., "Design and Optimization of Resonance-Based Efficient Wireless Power Delivery Systems for Biomedical Implants", IEEE Transactions on Biomedical Circuits and Systems, vol. 5, No. 1, Feb. 2011, pp. 48-63.

Randles, "Kinetics of rapid electrode reactions", Discussions of the Faraday Society, vol. 1, 1947, pp. 11-19.

Rategh et al., "Superharmonic Injection-Locked Frequency Dividers", IEEE Journal of Solid-State Circuits, vol. 34, No. 6, Jun. 1999, pp. 813-821.

Razavi, "Design of analog CMOS Integrated Circuits", McGraw-Hill Series in Electrical and Computer Engineering, 2001, 706 pgs., (Presented in 2 Parts).

Razavi, Behzad "RF Microelectronics", New Jersey: Prentice Hall, Chapter 8, vol. 1, 1998, pp. 497-594.

Rodriguez et al, "Long-term results of electrical stimulation of the lower esophageal sphincter for the treatment of gastroesophageal reflux disease", Endoscopy, vol. 45, No. 8, Aug. 2013, pp. 595-604, doi: 10.1055/s-0033-1344213.

Saluja et al., "A Supervised Machine Learning Algorithm for Heart-Rate Detection Using Doppler Motion-Sensing Radar", IEEE Journal of Electromagnetics, RF and Microwaves in Medicine and Biology, vol. 4, No. 1, Mar. 2020, First Published: Jun. 19, 2019, pp. 45-51, doi: 10.1109/JERM.2019.2923673.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554, DOI: 10.1109/TIE.2010.2046002.

Sankaragomathi et al., "A 27μw subcutaneous wireless biosensing platform with optical power and data transfer", Proceedings of the IEEE 2014 Custom Integrated Circuits Conference, Sep. 15, 2014, pp. 1-4.

Sayenko et al., "Spinal segment-specific transcutaneous stimulation differentially shapes activation pattern among motor pools in humans", Journal of Applied Physiology, vol. 118, 2015, pp. 1364-1374, first published Mar. 26, 2015, doi: 10.1152/japplphysiol.01128.2014.

Shi et al., "A 10 mm3 Inductive Coupling Radio for Syringe-Implantable Smart Sensor Nodes", IEEE Journal of Solid-State Circuits, vol. 51, No. 11, Nov. 2016, pp. 2570-2583, doi: 10.1109/JSSC.2016.2606162.

Shi et al., "A 10mm3 syringe-implantable near-field radio system on glass substrate", IEEE Int. Solid-State Circuits Conf. (ISSCC) Dig. Tech. Papers, Feb. 2016, pp. 448-449.

Silvetti et al., "Cardiac pacing in paediatric patients with congenital heart defects: transvenous or epicardial?", Europace, vol. 15, No. 9, Sep. 2013, published online Feb. 24, 2013, pp. 1280-1286, doi: 10.1093/europace/eut029.

Soontornpipit, "Design of an Implantable Antenna Feasibility Study for Continuous Glucose Monitoring", ECTI Transactions on Electrical Engineering, Electronics, and Communications, vol. 12, No. 1, Feb. 2014, pp. 44-52.

Stoopman et al., "Co-Design of a CMOS Rectifier and Small Loop Antenna for Highly Sensitive RF Energy Harvesters", IEEE Journal of Solid-State Circuits, vol. 49, No. 3, Mar. 2014, pp. 622-634, doi: 10.1109/JSSC.2014.2302793.

Sun et al., "A Two-Hop Wireless Power Transfer System with an Efficiency-Enhanced Power Receiver for Motion-Free Capsule Endoscopy Inspection", IEEE Transactions on Biomedical Engineering,

(56) References Cited

OTHER PUBLICATIONS vol. 59, No. 11, Nov. 2012, published online Jun. 29, 2012, pp. 3247-3254. doi: 10.1109/TBME.2012.2206809.
Sun et al., “A wirelessly powered injection-locked oscillator with on-chip antennas in 180nm SOI CMOS”, 2016 IEEE MTT-S International Microwave Symposium (IMS), Aug. 11, 2016, pp. 1-3 [online], [retrieved on Aug. 14, 2020]. Retrieved from the Internet <URL: https://ieeexplore .ieee.org/abstract/document/7540249>, entire document.
Sun et al., “A Wirelessly Powered Injection-Locked Oscillator With On-Chip Antennas in 180-nm SOI CMOS for Spectroscopy Application”, IEEE Sensors Letters, vol. 3, No. 7, Jul. 3, 2019, pp. 1-4 [online], [retrieved on Aug. 14, 2020]. Retrieved from the Internet <URL: https://ieeexplore.ieee.org/abstract/document/8754750>.
Sun et al., “Wirelessly powered implantable pacemaker with on-chip antenna”, 2017 IEEE MTT-S International Microwave Symposium (IMS), Jun. 4-9, 2017, pp. 1242-1244, doi: 10.1109/MWSYM.2017.8058831.
Tabesh et al., “A Power-Harvesting Pad-Less Millimeter-Sized Radio”, IEEE Journal of Solid-State Circuits, vol. 50, No. 4, Apr. 2015, pp. 962-977, doi: 10.1109/JSSC.2014.2384034.
Teh et al., “Design and analysis of UHF micropower CMOS DTMOST rectifiers”, IEEE Transactions on Circuits and Systems—II: Express Briefs, vol. 56, No. 2, Feb. 2009, pp. 122-126, doi: 10.1109/TCSII.2008.2010190.
Theilmann et al., “A µW Complementary Bridge Rectifier With Near Zero Turn-on Voltage in SOS CMOS for Wireless Power Supplies”, IEEE.
Transactions on Circuits and Systems I: Regular Papers, 2012, vol. 59, No. 9, Sep. 2012, pp. 2111-2124, doi: 10.1109/TCSI.2012.2185293.
Tjong et al., “Permanent Leadless Cardiac Pacemaker Therapy: A Comprehensive Review”, Circulation, vol. 135, No. 15, Apr. 11, 2017, pp. 1458-1470, doi: 10.1161/CirculationAHA.116.025037.
Tolosa et al., “Electrochemically deposited iridium oxide reference electrode integrated with an electroenzymatic glutamate sensor on a multi-electrode array microprobe”, Biosensors and Bioelectronics, vol. 42, Apr. 15, 2013, Available online Nov. 6, 2012, pp. 256-260, doi: 10.1016/jbios.2012.10.061.
Vakili et al., “Time-Domain System for Millimeter-Wave Material Characterization”, IEEE Transactions on Microwave Theory and Techniques, vol. 63, No. 9, Sep. 2015, First Published: Jul. 14, 2015, pp. 2915-2922, doi: 10.1109/TMTT.2015.2449833.
Van Dongen et al., “Does a coupling capacitor enhance the charge balance during neural stimulation? An empirical study”, Medical & Biological Engineering and Computing, 2016, vol. 54, pp. 93-101, published online May 29, 2015, doi: 10.1007/s11517-015-1312-9.
Van Rees et al., “Implantation-related complications of implantable cardioverter-defibrillators and cardiac resynchronization therapy devices: a systematic review of randomized clinical trials”, Journal of the American College of Cardiology, vol. 58, No. 10, Aug. 30, 2011, pp. 995-1000, doi: 10.1016/j.jacc.2011.06.007.
Wan et al., “Analysis and Design of a Thermoelectric Energy Harvesting System with Reconfigurable Array of Thermoelectric Generators for IoT Applications”, IEEE Transactions on Circuits and Systems I: Regular Papers, vol. 64, No. 9, Sep. 2017, pp. 2346-2358, doi: 10.1109/TCSI.2017.2708763.
Wang et al., “17.6 Rapid and energy-efficient molecular sensing using dual mm-Wave combs in 65nm CMOS: A 220-to-320GHz spectrometer with 5.2mW radiated power and 14.6-to-19.5dB noise figure”, 2017 IEEE International Solid-State Circuits Conference (ISSCC), Feb. 5-9, 2017, San Francisco, CA, USA, pp. 302-303, doi: 10.1109/ISSCC.2017.7870381.
Wang et al., “Dual-Terahertz-Comb Spectrometer on CMOS for Rapid, Wide-Range Gas Detection With Absolute Specificity”, IEEE Journal of Solid-State Circuits, vol. 52, No. 12, Dec. 2017, First Published: Oct. 16, 2017, pp. 3361-3372, doi: 10.1109/JSSC.2017.2755693.
Weber et al., “A Miniaturized Single-Transducer Implantable Pressure Sensor With Time-Multiplexed Ultrasonic Data and Power Links”, IEEE Journal of Solid-State Circuits, vol. 53, No. 4, Apr. 2018, pp. 1089-1101, doi: 10.1109/JSSC.2017.2782086.
Weber et al., “Functional electrical stimulation using microstimulators to correct foot drop: a case study1”, Canadian Journal of Physiology and Pharmacology, vol. 82, No. 8-9, first published Oct. 19, 2004, pp. 784-792, doi: 10.1139/Y04-078.
Weiss et al., “One-Shot Learning for Robust Material Classification Using Millimeter-Wave Radar System”, IEEE Sensors Letters, vol. 2, No. 4, Dec. 2018, First Published: Oct. 25, 2018, pp. 1-4, doi: 10.1109/LSENS.2018.2878041.
Wu et al., “25.3 a 40-to-330GHz synthesizer-free THz spectroscope-on-chip exploiting electromagnetic scattering”, 2016 IEEE International Solid-State Circuits Conference (ISSCC), Jan. 31-Feb. 4, 2016, San Francisco, CA, USA, pp. 428-429, doi: 10.1109/ISSCC.2016.7418090.
Wu et al., “On-Chip THz Spectroscope Exploiting Electromagnetic Scattering With Multi-Port Antenna”, IEEE Journal of Solid-State Circuits, vol. 51, No. 12, Dec. 2016, First Published Sep. 2, 2016, pp. 3049-3062, doi: 10.1109/JSSC.2016.2597845.
Xie et al., “Wireless power transfer and applications to sensor networks”, IEEE Wireless Communications, vol. 20, No. 4, Aug. 2013, pp. 140-145, doi: 10.1109/MWC.2013.6590061.
Xu et al., “A Fully Implantable Stimulator with Wireless Power and Data Transmission for Experimental Investigation of Epidural Spinal Cord Stimulation”, IEEE Transactions on Neural Systems and Rehabilitation Engineering, vol. 23, No. 4, 2015, pp. 683-692, doi: 10.1109/TNSRE.2015.2396574.
Yadav et al., “Low Voltage Low Power Sub-threshold Operational Amplifier in 180nm CMOS”, 2017 IEEE Third International Conference on Sensing, signal Processing and Security (ICSSS), 2017, 4 pgs.
Yakovlev et al., “An 11 µW Sub-pJ/bit Reconfigurable Transceiver for mm-Sized Wireless Implants”, IEEE Transactions on Biomedical Circuits and Systems, vol. 10, No. 1, Sep. 2013, 4 pgs., doi: 10.1109/CICC.2013.6658501.
Yi et al., “Analysis And Design Strategy of UHF Micro-Power CMOS Rectifiers for Micro-Sensor and RFID Applications”, IEEE Transactions on Circuits and Systems I: Regular Papers, vol. 54, No. 1, Jan. 15, 2007, pp. 153-166, doi: 10.1109/TCSI.2006.887974.
Yu et al., “Cardiac resynchronization therapy: state of the art 2013”, European Heart Journal, vol. 34, No. 19, May 14, 2013, online published Jan. 25, 2013, pp. 1396-1403, doi: 10.1093/eurheartj/ehs454.
Yvanoff et al., “A Feasibility Study of Tissue Characterization Using Implanted LC Sensors”, IEEE Transactions on Antennas and Propagation, vol. 57, No. 4, Apr. 2009, pp. 885-893, doi: 10.1109/TAP.2009.2016073.
Zargham et al., “Fully Integrated On-Chip Coil in 0.13 µm CMOS for Wireless Power Transfer Through Biological Media”, IEEE Transactions on Biomedical Circuits and Systems, vol. 9, No. 2, Apr. 2015, pp. 259-271, doi: 10.1109/TBCAS.2014.2328318.
Zhang et al., “A 23 µA RF-Powered Transmitter for Biomedical Applications”, IEEE Radio Frequency Integrated Circuits Symposium, 2011, 4 pgs., doi: 10.1109/RFIC.2011.5940711.
Zhang et al., “A Miniature Mode Reconfigurable Inductorless IR-UWB Transmitter—Receiver for Wireless Short-Range Communication and Vital-Sign Sensing”, IEEE Journal of Emerging and Selected Topics in Circuits and Systems, vol. 8, No. 2, Jun. 2018, pp. 294-305.
International Preliminary Report on Patentability for International Application No. PCT/US2022/081388, Report issued Jun. 20, 2024, Mailed on Jul. 11, 2024, 18 pgs.
International Preliminary Report on Patentability for International Application No. PCT/US2023/073562, Report issued Mar. 1, 2025, Mailed Mar. 20, 2025, 12 pgs.
International Search Report and Written Opinion for International Application No. PCT/US2023/073562, Search completed Jan. 29, 2024, Mailed Feb. 28, 2024, 13 pgs.
Andersen et al., “A 118-mW Pulse-Based Radar SoC in 55-nm CMOS for Non-Contact Human Vital Signs Detection”, IEEE Journal of Solid-State Circuits, vol. 52, No. 12, Dec. 2017, pp. 3421-3433, doi: 10.1109/JSSC.2017.2764051.

(56) References Cited

OTHER PUBLICATIONS

Ardell et al., "Central-peripheral neural network interactions evoked by vagus nerve stimulation: functional consequences on control of cardiac function", American Journal of Physiology—Heart and Circulatory Physiolog, vol. 309, No. 10, Nov. 2015, pp. H1740-H1752, doi: 10.1152/ajpheart.00557.2015.

Besnoff et al., "Battery-free multichannel digital ECG biotelemetry using UHF RFID techniques", 2013 IEEE International Conference on RFID, 2013, pp. 16-22.

Bourdel et al., "A 9-pJ/pulse 1.42-Vpp OOK CMOS UWB pulse generator for the 3.1-10.6-GHz FCC band", IEEE Transactions on Microwave Theory and Techniques, vol. 58, No. 1, 2009, pp. 65-73.

Chae et al., "A 128-channel 6 mW wireless neural recording IC with spike feature extraction and UWB transmitter", IEEE Transactions on Neural Systems and Rehabilitation Engineering, vol. 17, No. 4, 2009, pp. 312-321.

Choi et al., "A Wirelessly Powered Microspectrometer for Neural Probe-Pin Device.", Proceedings of SPIE, Micro+Nano Materials, Devices, and Systems, vol. 9668, 2015, 8 pgs., doi: 10.1117/12.2202203.

Cruz et al., "Hybrid UHF/UWB Antenna for Passive Indoor Identification and Localization Systems", IEEE Transactions on Antennas and Propagation, vol. 61, No. 1, Jan. 2013, pp. 354-361, doi: 10.1109/TAP.2012.2220112.

Jang et al., "Wirelessly Powered, Batteryless Closed-loop Biopotential Recording IC for Implantable Leadless Cardiac Monitoring Applications", IEEE Biomedical Circuits and Systems Conference (BioCAS), 2021, pp. 1-4, doi: 10.1109/BioCAS49922.2021.9644988.

Jia et al., "A Trimodal Wireless Implantable Neural Interface System-on-Chip", IEEE International Solid-State Circuits Conference—(ISSCC), 2020, pp. 414-416, doi: 10.1109/ISSCC19947.2020.9063065.

Koski et al., "Fundamental Characteristics of Electro-Textiles in Wearable UHF RFID Patch Antennas for Body-Centric Sensing Systems", IEEE Transactions on Antennas and Propagation, vol. 62, No. 12, Dec. 2014, Date of Publication: Oct. 20, 2014, pp. 6454-6462.

Lu et al., "Performance Evaluation of a Long-Range RFID Tag Powered by a Vibration Energy Harvester", IEEE Antennas and Wireless Propagation Letters, vol. 16, 2017, pp. 1832-1835.

Lyu et al., "A 100-M/s 2.6-pJ/pulse compact UWB impulse transmitter based on antenna-and-pulsegenerator codesign", IEICE Electronics Express, vol. 16, No. 24, 20190672, 2019, 4 pgs., doi: 10.1587/elex.16.20190672.

Lyu et al., "A 915-MHz Far-Field Energy Harvester with-22-dBm Sensitivity and 3-V Output Voltage Based on Antenna-and-Rectifier Codesign", IEEE Microwave and Wireless Components Letters, vol. 29, No. 8, Aug. 2019, pp. 557-559, doi: 10.1109/LMWC.2019.2923685.

Marrocco, "The Art of UHF RFID Antenna Design: Impedance-Matching and Size-Reduction Techniques", IEEE Antennas and Propagation Magazine, vol. 50, No. 1, Feb. 2008, pp. 66-79.

Moiz et al., "An Embedded Multichannel Telemetry Unit for Bone Strain Monitoring", EURASIP Journal on Embedded Systems, vol. 2013, No. 1, Article 14, Oct. 17, 2013, 16 pgs., doi: 10.1186/1687-3963-2013-14.

Nikitin et al., "Power Reflection Coefficient Analysis for Complex Impedances in RFID Tag Design", IEEE Transactions on Microwave Theory and Techniques, vol. 53, No. 9, Sep. 2005, pp. 2721-2725, doi: 10.1109/TMTT.2005.854191.

Occhiuzzi et al., "Modeling, Design and Experimentation of Wearable RFID Sensor Tag", IEEE Transactions on Antennas and Propagation, vol. 58, No. 8, Aug. 2010, pp. 2490-2498, doi: 10.1109/TAP.2010.2050435.

Piech et al., "A wireless millimetre-scale implantable neural stimulator with ultrasonically powered bidirectional communication", Nature Biomedical Engineering, vol. 4, No. 2, Feb. 2020, first published Feb. 19, 2020, pp. 207-222, doi: 10.1038/s41551-020-0518-9.

Riaz et al., "A Novel Design of UHF RFID Passive Tag Antenna Targeting Smart Cards Limited Area", 2018 IEEE International Conference on Consumer Electronics (ICCE), 2018, 4 pgs.

Schleicher et al., "IR-UWB Radar Demonstrator for Ultra-Fine Movement Detection and Vital-Sign Monitoring", IEEE Transactions on Microwave Theory and Techniques, vol. 61, No. 5, May 2013, pp. 2076-2085, doi: 10.1109/TMTT.2013.2252185.

Tan et al., "A 1.2-V 8.3-nJ CMOS Humidity Sensor for RFID Applications", IEEE Journal of Solid-State Circuits, vol. 48, No. 10, Oct. 2013, pp. 2469-2477, doi: 10.1109/JSSC.2013.2275661.

Vaz et al., "Full Passive UHF Tag With a Temperature Sensor Suitable for Human Body Temperature Monitoring", IEEE Transactions on Circuits and Systems II: Express Briefs, vol. 57, No. 2, Feb. 2010, pp. 95-99, doi: 10.1109/TCSII.2010.2040314.

Wang et al., "Single-antenna Doppler radars using self and mutual injection locking for vital sign detection with random body movement cancellation", IEEE Transactions on Microwave Theory and Techniques, vol. 59, No. 12, Dec. 2011, pp. 3577-3587, doi: 10.1109/TMTT.2011.2171712.

Yang et al., "Wearable RFID-Enabled Sensor Nodes for Biomedical Applications", 58th Electronic Components and Technology Conference, 2008, pp. 2156-2159.

Yeager et al., "A 9 μA, Addressable Gen2 Sensor Tag for Biosignal Acquisition", IEEE Journal of Solid-State Circuits, vol. 45, No. 10, Oct. 2010, pp. 2198-2209, doi: 10.1109/JSSC.2010.2063930.

Yu et al., "Multisite bio-stimulating implants magnetoelectrically powered and individually programmed by a single transmitter", IEEE Custom Integrated Circuits Conference (CICC), 2021, pp. 1-2, doi: 10.1109/CICC51472.2021.9431457.

Lyu et al., "A 13.56-mhz-25-dbm-sensitivity inductive power receiver system-on-a-ship with a self-adaptive successive approximation resonance compensation front-end for ultra-low-power medical implants", IEEE Transaction on Biomedical Circuits and Systems, 2000, vol. 15, pp. 80-90.

Extended European Search Report dated Jul. 19, 2022, issued in related European Application No. 19887763.1, 7 pgs.

Extended European Search Report for European Application No. 20860681.4, Search completed Jul. 26, 2023, Mailed Aug. 2, 2023, 7 pgs.

Extended European Search Report for European Application No. 21759630.3, Search completed Apr. 2, 2024, Mailed Apr. 12, 2024, 8 pgs.

Extended European Search Report for European Application No. 20866392.2, Search completed Aug. 31, 2023, Mailed Sep. 11, 2023, 5 pgs.

International Preliminary Report on Patentability dated Sep. 22, 2022, issued in related International Application PCT/US2021/021467, 6 pgs.

International Preliminary Report on Patentability for International Application PCT/US2021/020343, Report issued Aug. 30, 2022, Mailed on Sep. 9, 2022, 7 pgs.

International Preliminary Report on Patentability for International Application No. PCT/US2022/071066, Report issued Sep. 12, 2023, Mailed Sep. 21, 2023, 9 pgs.

International Preliminary Report on Patentability for International Application PCT/US2019/059657, Report issued May 25, 2021, Mailed on Jun. 3, 2021, 8 pgs.

International Preliminary Report on Patentability for International Application PCT/US2019/062443, Report issued May 25, 2021, Mailed Jun. 3, 2021, 7 pgs.

International Preliminary Report on Patentability for International Application PCT/US2020/015461, Report issued Jul. 27, 2021, Mailed on Aug. 12, 2021, 13 pgs.

International Preliminary Report on Patentability for International Application PCT/US2020/040283, Report issued Jan. 11, 2022, Mailed on Jan. 20, 2022, 7 pgs.

International Preliminary Report on Patentability for International Application PCT/US2020/041007, Report issued Jan. 11, 2022, Mailed on Jan. 20, 2022, 6 pgs.

International Preliminary Report on Patentability for International Application PCT/US2020/048001, Report issued Mar. 15, 2022, Mailed on Mar. 31, 2022, 6 pgs.

(56) References Cited

OTHER PUBLICATIONS

International Preliminary Report on Patentability for International Application PCT/US2021/073036, Report issued Jun. 13, 2023, Mailed on Jun. 29, 2023, 10 pgs.
International Preliminary Report on Patentability for International Application PCT/US2023/060569, Report issued Jun. 20, 2024, Mailed on Jul. 25, 2024, 8 pgs.
International Search Report and Written Opinion for Application PCT/US2021/35132, completed Aug. 2, 2021, mailed Oct. 4, 2021, 10 pgs.
International Search Report and Written Opinion for International Application No. PCT/US2022/081388, Search completed Mar. 6, 2023, Mailed Mar. 21, 2023, 24 pgs.
International Search Report and Written Opinion for International Application No. PCT/US2019/059657, Search completed Dec. 31, 2019, Mailed Jan. 21, 2020, 12 pgs.
International Search Report and Written Opinion for International Application No. PCT/US2019/062443, Search completed Jan. 15, 2020, Mailed Jan. 29, 2020, 15 pgs.
International Search Report and Written Opinion for International Application No. PCT/US2020/040283, Search completed Aug. 17, 2020, Mailed Sep. 28, 2020, 17 pgs.
International Search Report and Written Opinion for International Application No. PCT/US2020/041007; Search completed Aug. 29, 2020, Mailed Oct. 2, 2020,13 pgs.
International Search Report and Written Opinion for International Application No. PCT/US2020/048001, Search completed Oct. 17, 2020, Mailed Nov. 20, 2020, 12 pgs.
International Search Report and Written Opinion for International Application No. PCT/US2021/020343, Search completed Jun. 2, 2021, Mailed Jun. 22, 2021, 13 pgs.
International Search Report and Written Opinion for International Application No. PCT/US2021/073036, Search completed Apr. 14, 2022, Mailed May 3, 2022, 18 pgs.
International Search Report and Written Opinion for International Application No. PCT/US2022/036926, Search completed Sep. 8, 2022, Mailed Oct. 17, 2022, 7 pgs.
International Search Report and Written Opinion for International Application No. PCT/US2022/071066, Search completed Jun. 21, 2022, Mailed Jul. 5, 2022, 21 pgs.
International Search Report and Written Opinion for International Application No. PCT/US2022/077550, Search completed Dec. 31, 2022, Mailed Feb. 2, 2023, 18 pgs.
International Search Report and Written Opinion for International Application PCT/US2017/0047901, filed Aug. 22, 2017, 13 pgs.
International Search Report and Written Opinion for International Application PCT/US2017/052163, filed Sep. 19, 2017, 13 pgs.
International Search Report and Written Opinion for International Application PCT/US2020/015461, Report Completed Mar. 30, 2020, Mailed May 21, 2020, 19 pgs.
International Search Report and Written Opinion for International Application PCT/US2020/049349, mailed Nov. 24, 2020, 7 pgs.
International Search Report and Written Opinion for International Application PCT/US2021/21467, Mailed Jun. 3, 2021, 9 pgs.
Abbasi et al., "Single-Chip 220-GHz Active Heterodyne Receiver and Transmitter MMICs With On-Chip Integrated Antenna", IEEE Transactions on Microwave Theory and Techniques, vol. 59, No. 2, Feb. 2011, pp. 466-478, doi: 10.1109/tmtt.2010.2095028.
Abiri et al., "Inductively powered wireless pacing via a miniature pacemaker and remote stimulation control system", Science Reports, vol. 7, No. 6180, Jul. 21, 2017, pp. 1-10, doi: 10.1038/s41598-017-06493-5.
Agarwal et al., "A 4μW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.
Ahn et al., "Optimal Design of Wireless Power Transmission Links for Millimeter-Sized Biomedical Implants", IEEE Transactions on Biomedical Circuits and Systems, vol. 10, No. 1, Feb. 2016, pp. 125-137, doi: 10.1109/TBCAS.2014.2370794.
Akin et al., "A Telemetrically Powered and Controlled Implantable Neural Recording System with CMOS Interface Circuitry", Proceedings of the Mediterranean Electrotechnical Conference . Antalya, Turkey, New York, IEEE, US, vol. 2, No. ISBN: 978-0-7803-1772-6, Apr. 12, 1994, pp. 545-548, XP000506184.
Al Hadi et al., "A 1 k-Pixel Video Camera for 0.7-1.1 Terahertz Imaging Applications in 65-nm CMOS", IEEE Journal of Solid-State Circuits, vol. 47, No. 12, Dec. 2012, First Published: Dec. 2012, pp. 2999-3012, doi: 10.1109/JSSC.2012.2217851.
Arfin et al., "An energy-efficient, adiabatic electrode stimulator with inductive energy recycling and feedback current regulation", IEEE Transactions on Biomedical Circuits and Systems, vol. 6, No. 1, Feb. 2012, pp. 1-14, first published Oct. 6, 2011, doi: 10.1109/TBCAS.2011.2166072.
Atzori et al., "The Internet of Things: A survey", Computer Networks, vol. 54, No. 15, Oct. 2010, pp. 2787-2805, doi: 10.1016/j.comnet.2010.05.010.
Bahrami et al., "Flexible, polarization-diverse UWB antennas for implantable neural recording systems", IEEE Transactions on Biomedical Circuits and Systems, vol. 10, No. 1, Feb. 2016, pp. 38-48, doi: 10.1109/tbcas.2015.2393878.
Bahrami et al., "System Level Design of a Full-Duplex Wireless Transceiver for Brain-Machine Interfaces", IEEE Transactions on Microwave Theory and Techniques, vol. 64, No. 10, Oct. 2016, 10 pgs., doi: 10.1109/tmtt.2016.2600301.
Balanis, Constantine A. "Antenna Theory: Analysis and Design", John Wiley & Sons, 2016, 1095 pgs. (Presented in 4 Parts).
Bereuter et al., "Hot Topic in Cardiac Devices—Leadless cardiac dual-chamber pacing", Europace Abstracts Supplement, 2018, 1 pg., doi: 10.1093/europace/euy015.
Bereuter et al., "Leadless Dual-Chamber Pacing, A Novel Communication Method for Wireless Pacemaker Synchronization", JACC: Basic to Translational Service, vol. 3, No. 6, Dec. 2018, pp. 813-823, doi: 10.1016/j.jacbts.2018.07.009.
Biederman et al., "A Fully-Integrated, Miniaturized (0.125 $mm^2$) 10.5 μW Wireless Neural Sensor", IEEE Journal of Solid-State Circuits, vol. 48, No. 4, Apr. 2013, pp. 960-970, doi: 10.1109/JSSC.2013.2238994.
Bigio et al., "Microwave absorption spectroscopy of DNA", Biopolymers, vol. 33, No. 1, Jan. 1993, pp. 147-150, doi: 10.1002/bip.360330114.
Bourdel et al., "A 9-pJ/Pulse 1.42-Vpp OOK CMOS UWB Pulse Generator for the 3.1-10.6-GHz FCC Band", IEEE Transactions on Microwave Theory and Techniques, vol. 58, No. 1, Jan. 2010, pp. 1-9, doi: 10.1109/tmtt.2009.2035959.
Brown et al., "An Ultra-Low-Power 9.8 GHz Crystal-Less UWB Transceiver With Digital Baseband Integrated in 0.18 μm BiCMOS", IEEE International Solid-State Circuits Conference, 2013, pp. 442-443, doi: 10.1109/isscc.2013.6487806.
Carlson et al., "A 20 mV Input Boost Converter With Efficient Digital Control for Thermoelectric Energy Harvesting", IEEE Journal of Solid-State Circuits, vol. 45, No. 4, Apr. 2010, pp. 741-750, doi: 10.1109/jssc.2010.2042251.
Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321, doi: 10.1109/TNSRE.2009.2021607.
Chang et al., "27.7 a 30.5mm3 fully packaged implantable device with duplex ultrasonic data and power links achieving 95kb/s with <10-4 BER at 8.5cm depth", IEEE International Solid-State Circuits Conference (ISSCC), Feb. 5-9, 2017, pp. 460-461, doi: 10.1109/ISSCC.2017.7870460.
Charthad et al., "A mm-sized implantable medical device (IMD) with ultrasonic power transfer and a hybrid bi-directional data link", IEEE Journal of Solid-State Circuits, vol. 50, No. 8, Aug. 2015, pp. 1741-1753, doi: 10.1109/JSSC.2015.2427336.
Charthad et al., "A mm-Sized Wireless Implantable Device for Electrical Stimulation of Peripheral Nerves", IEEE Transactions on Biomedical Circuits and Systems, vol. 12, No. 2, Apr. 2018, pp. 257-270, doi: 10.1109/TBCAS.2018.2799623.
Charthad et al., "System-Level Analysis of Far-Field Radio Frequency Power Delivery for mm-Sized Sensor Nodes", IEEE Trans-

(56) References Cited

OTHER PUBLICATIONS actions on Circuits and Systems I: Regular Papers, vol. 63, No. 2, Feb. 3, 2016, pp. 300-311, doi: 10.1109/TCSI.2015.2512720.
Chen et al., "3D Radar Imaging based on a Synthetic Array of 30GHz Impulse Radiators with On-Chip Antennas in 130nm SiGe BiCMOS", IEEE Transactions on Microwave Theory and Techniques, vol. 65, No. 11, Nov. 2017, pp. 4373-4384, doi: 10.1109/TMTT.2017.2694826.
Chen et al., "Multiple leadless pacemakers implanted in the right ventricle of swine", Europace, vol. 18, No. 11, 2016, pp. 1748-1752, published online Jan. 31, 2016, doi: 10.1093/europace/euv418.
Cheng, "Field and wave electromagnetics", Pearson Education India, 1989, 720 pgs.
Chinitz et al., "Accelerometer-based atrioventricular synchronous pacing with a ventricular leadless pacemaker: Results from the Micra atrioventricular feasibility studies", Heart Rhythm, vol. 15, No. 9, Sep. 2018, pp. 1363-1371, doi: 10.1016/j.hrthm.2018.05.004.
Cogan, "Neural stimulation and recording electrodes", Annual Review of Biomedical Engineering, vol. 10, No. 1, 2008, pp. 275-309, first published online Apr. 22, 2008, doi: 10.1146/annurev.bioeng.10.061807.160518.
Cogan et al., "Potential-biased, asymmetric waveforms for charge-injection with activated iridium oxide (AIROF) neural stimulation electrodes", IEEE Transactions on Biomedical Engineering, vol. 53, No. 2, Feb. 2006, first published Jan. 23, 2006, pp. 327-332, doi: 10.1109/TBME.2005.862572.
Dagan et al., "A low-power low-cost 24 ghz rfid tag with a c-flash based embedded memory", IEEE Journal of Solid-State Circuits, vol. 49, No. 9, Sep. 2014, pp. 1942-1957, doi: 10.1109/JSSC.2014.2323352.
Dagdeviren et al., "Conformal piezoelectric energy harvesting and storage from motions of the heart, lung, and diaphragm", PNAS, vol. 111, No. 5, Feb. 4, 2014, published online Jan. 21, 2014, pp. 1927-1932, doi: 10.1073/pnas.1317233111.
Daubert et al., "2012 EHRA/HRS expert consensus statement on cardiac resynchronization therapy in heart failure: implant and follow-up recommendations and management", Heart Rhythm, vol. 9, No. 9, Sep. 1, 2012, pp. 1524-1576, doi: 10.1016/j.hrthm.2012.07.025.
De Roover et al., "A fully integrated wireless power supply for pinless active RFID-devices in 130nm CMOS", 2007 IEEE Asian Solid-State Circuits Conference, Nov. 12-14, 2007, pp. 123-126, doi: 10.1109/ASSCC.2007.4425747.
Deer et al., "The Appropriate Use of Neurostimulation: Avoidance and Treatment of Complications of Neurostimulation Therapies for the Treatment of Chronic Pain", Neuromodulation: Technology at the Neural Interface, vol. 17, No. 6, Aug. 12, 2014, pp. 571-598, doi: 10.1111/ner.12206.
Derksen et al., "Tissue Discontinuities Affect Conduction Velocity Restitution", Circulation, vol. 108, No. 7, Aug. 19, 2003, pp. 882-888, doi: 10.1161/01.CIR.0000081766.16185.28.
Dickson, "On-chip high-voltage generation in MNOS integrated circuits using an improved voltage multiplier technique", IEEE Journal of Solid-State Circuits, vol. 11, No. 3, 1976, pp. 374-378, doi: 10.1109/JSSC.1976.1050739.
Ding et al., "Inattentive Driving Behavior Detection Based on Portable FMCW Radar", IEEE Transactions on Microwave Theory and Techniques, vol. 67, No. 10, Oct. 2019, First Published: Aug. 27, 2019, pp. 4031-4041, doi: 10.1109/TMTT.2019.2934413.
Dorta-Quinones et al., "A Wireless FSCV Monitoring IC With Analog Background Subtraction and UWB Telemetry", IEEE Transactions on Biomedical Circuits and Systems, vol. 10, No. 2, Apr. 2016, pp. 289-299, doi: 10.1109/tbcas.2015.2421513.
Dosdall et al., "Mechanisms of defibrillation", Annual Review of Biomedical Engineering, vol. 12, Aug. 15, 2010, first published as a Review in Advance May 5, 2010, pp. 233-258, doi: 10.1146/annurev-bioeng-070909-105305.
Eldeeb et al., "A 0.4-V Miniature CMOS Current Mode Instrumentation Amplifier", IEEE Transactions on Circuits and Systems—II Express Briefs, Mar. 2018, vol. 65, No. 3, pp. 261-265, doi: 10.1109/TCSII.2017.2685589.
FCC, "First Report and Order 02-48", Federal Communication Commission (FCC), Feb. 2002, 118 pgs.
Fenton et al., "Termination of Atrial Fibrillation Using Pulsed Low-Energy Far-Field Stimulation", Circulation, vol. 120, No. 6, Aug. 11, 2009, pp. 467-476, first published Jul. 27, 2009, doi: 10.1161/CirculationAHA.108.825091.
Gao et al., "A 71GHz RF Energy Harvesting Tag with 8% Efficiency for Wireless Temperature Sensors in 65nm CMOS", IEEE Radio Frequency Integrated Circuits Symposium (RFIC), Jun. 2013, pp. 403-406, doi: 10.1109/RFIC.2013.6569616.
Gilbert, "Impedance matching with lossy components", IEEE Transactions on Circuits and Systems, vol. 22, No. 2, Feb. 1975, pp. 96-100, doi: 10.1109/TCS.1975.1084016.
Glaab et al., "Terahertz heterodyne detection with silicon field-effect transistors", Applied Physics Letters, vol. 96, No. 4, Article 042106, Jan. 27, 2010, pp. 042106-1-042106-3, doi: 10.1063/1.3292016.
Grenier et al., "Recent advances in microwave-based dielectric spectroscopy at the cellular level for cancer investigations", IEEE Transactions on Microwave Theory and Techniques, vol. 61, No. 5, Apr. 11, 2013, pp. 2023-2030, doi: 10.1109/TMTT.2013.2255885.
Guler et al., "Power Management in Wireless Power-Sipping Devices: A Survey", IEEE Circuits and Systems Magazine, vol. 17, No. 4, Nov. 20, 2017, pp. 64-82, doi: 10.1109/MCAS .2017.2757090.
Gunturi et al., "A 250-Mb/s Data Rate IR-UWB Transmitter Using Current-Reused Technique", IEEE Transactions on Microwave Theory and Techniques, vol. 65, No. 11, Nov. 2017, pp. 4255-4265, doi: 10.1109/TMTT.2017.2695189.
Habibagahi et al., "Miniaturized Wirelessly Powered and Controlled Implants for Vagus Nerve Stimulation", IEEE Radio Frequency Integrated Circuits Symposium (RFIC), Date of Conference Jun. 19-21, 2022, Denver, CO, pp. 51-54, doi: 10.1109/RFIC54546.2022.9863172.
Habibagahi et al., "Vagus nerve stimulation using a miniaturized wirelessly powered stimulator in pigs", Scientific Reports, vol. 12, No. 8184, May 17, 2022, 12 pgs., doi: 10.1038/s41598-022-11850-0.
Hagen et al., "Multimodal Modeling of Neural Network Activity: Computing LFP, ECoG, EEG, and MEG Signals With LFPy 2.0", Frontiers in Neuroinformatics, vol. 12, No. 92, 2018, 36 pgs., doi: 10.3389/fninf.2018.00092.
Hannan et al., "Energy harvesting for the implantable biomedical devices: issues and challenges", BioMedical Engineering OnLine, vol. 13, No. 79, 2014, 23 pgs., doi: 10.1186/1475-925X-13-79.
Harrison, Reid "The Design of Integrated Circuits to Observe Brain Activity", Proceedings of the IEEE, vol. 96, No. 7, Jul. 2008, pp. 1203-1216, doi: 10.1109/jproc.2008.922581.
Hehn et al., "A Fully Autonomous Integrated Interface Circuit for Piezoelectric Harvesters", IEEE Journal of Solid-State Circuits, vol. 47, No. 9, Sep. 2012, pp. 2185-2198, doi: 10.1109/JSSC.2012.2200530.
Higgins et al., "Advances in Pacing Therapy: Examining the Potential Impact of Leadless Pacing Therapy", Journal of Innovations in Cardiac Rhythm Management, vol. 5, Nov. 2014, pp. 1825-1833, doi: 10.19102/icrm.2014.051106.
Ho et al., "Wireless power transfer to deep-tissue microimplants", PNAS, vol. 111, No. 22, Jun. 3, 2014, first published May 19, 2014, pp. 7974-7979, doi: 10.1073/pnas.1403002111.
Huang et al., "A 1-μW 10-bit 200-kS/s SAR ADC With a Bypass Window for Biomedical Applications", IEEE Journal of Solid-State Circuits, vol. 47, No. 11, Nov. 2012, pp. 2783-2795, doi: 10.1109/jssc.2012.2217635.
Huang et al., "A simple subthreshold cmos voltage reference circuit with channel-length modulation compensation", IEEE Transactions on Circuits and Systems—II: Express Briefs, vol. 53, No. 9, Sep. 2006, pp. 882-885, doi: 10.1109/TCSII.2006.881813.

(56) References Cited

OTHER PUBLICATIONS

Huang et al., "Materials and designs for wireless epidermal sensors of hydration and strain", Advanced Functional Materials, vol. 24, No. 25, Jul. 2, 2014, pp. 3846-3854, first published Mar. 2, 2014, doi: 10.1002/adfm.201303886.
Huang et al., "Neurostimulation Strategy for Stress Urinary Incontinence", IEEE Transactions on Neural Systems and Rehabilitation Engineering, vol. 25, No. 7, Jul. 2017, pp. 1068-1078, first published Mar. 7, 2017, doi: 10.1109/TNSRE.2017.2679077.
Jamali et al., "A Fully Integrated 50-280-GHz Frequency Comb Detector for Coherent Broadband Sensing", IEEE Transactions on Terahertz Science and Technology, vol. 9, No. 6, Nov. 2019, First Published: Sep. 26, 2019, pp. 613-623, DOI: 10.1109/TTHZ.2019.2944129.
Jawad et al., "Opportunities and Challenges for Near-Field Wireless Power Transfer: A Review", Energies, vol. 10, No. 1022, Jul. 18, 2017, 28 pgs., doi: 10.3390/en10071022.
Jeon et al., "A 143nW Glucose-Monitoring Smart Contact Lens IC with a Dual-Mode Transmitter for Wireless-Powered Backscattering and RF-Radiated Transmission Using a Single Loop Antenna", Symposium on VLSI Circuits, Jun. 9-14, 2019, pp. C294-C295, doi: 10.23919/VLSIC.2019.8777984.
Jia et al., "A mm-sized free-floating wirelessly powered implantable optical stimulating system-on-a-chip", 2018 IEEE International Solid-State Circuits Conference—(ISSCC), Feb. 11-15, 2018, San Francisco, CA, pp. 468-470, doi: 10.1109/ISSCC.2018.8310387.
Jiang et al., "25.5 a 320GHz subharmonic-mixing coherent imager in 0.13μm SiGe BiCMOS", 2016 IEEE International Solid-State Circuits Conference (ISSCC), Jan. 31-Feb. 4, 2016, San Francisco, CA, USA, pp. 432-434, doi: 10.1109/ISSCC.2016.7418092.
Jiang et al., "A Sub-1 μW Multiparameter Injectable BioMote for Continuous Alcohol Monitoring", IEEE Custom Integrated Circuits Conference (CICC), 2018, pp. 1-4.
Johnson et al., "StimDust: A 6.5 mm3, wireless ultrasonic peripheral nerve stimulator with 82% peak chip efficiency", UC Berkeley, Retrieved from https://escholarship.org/uc/item/8px811qc on Sep. 10, 2024, published Apr. 1, 2018, pp. 1-4, doi: 10.1109/CICC.2018.8357047.
Kang et al., "A 1.7×4.1×2 mm3 Fully Integrated pH Sensor for Implantable Applications Using Differential Sensing and Drift-Compensation", 2019 Symposium on VLSI Circuits Digest of Technical Papers, C25-1, pp. C310-C311.
Kang et al., "Design and Optimization of Area-Constrained Wirelessly Powered CMOS UWB SoC for localization applications", IEEE Transactions on Microwave Theory and Techniques, vol. 64, No. 4, Apr. 2016, pp. 1042-1054, doi: 10.1109/TMTT.2016.2536663.
Karthaus et al., "Fully Integrated Passive UHF RFID Transponder IC With 16.7-μW Minimum RF Input Power", IEEE Journal of Solid State Circuits, vol. 38, No. 10, Oct. 2003, pp. 1602-1608, doi: 10.1109/JSSC.2003.817249.
Kaya et al., "A CMOS Time Domain Microwave Broadband Dielectric Spectroscopy System with a Contact-less Sensor for Liquid Chemical Detection", 2019 IEEE MTT-S International Microwave Symposium (IMS), Jun. 2-7, 2019, Boston, MA, USA, pp. 800-803, doi: 10.1109/mwsym.2019.8700726.
Kelly et al., "A power-efficient neural tissue stimulator with energy recovery", IEEE Transactions on Biomedical Circuits and Systems, vol. 5, No. 1, Feb. 2011, pp. 20-29, first published Jan. 24, 2011, doi: 10.1109/TBCAS.2010.2076384.
Kennedy et al., "High intensity focused ultrasound: surgery of the future?", British Journal of Radiology, vol. 76, No. 909, Sep. 2003, pp. 590-599, doi: 10.1259/bjr/17150274.
Kim et al., "A 144-MHz Fully Integrated Resonant Regulating Rectifier With Hybrid Pulse Modulation for mm-Sized Implants", IEEE Journal of Solid-State Circuits, vol. 52, No. 11, Nov. 2017, pp. 3043-3055, doi: 10.1109/JSSC.2017.2734901.
Kim et al., "Design of miniaturized wireless power receivers for mm-sized implants", 2017 IEEE Custom Integrated Circuits Conference (CICC), Apr. 30-May 30, 2017, 8 pgs., doi: 10.1109/CICC.2017.7993703.
Kim et al., "Wireless power transfer to a cardiac implant", Applied Physics Letters, vol. 101, No. 7, 073701, Aug. 13, 2012, pp. 073701-1-073701-4; doi: 10.1063/1.4745600.
Knap et al., "Plasma wave detection of sub-terahertz and terahertz radiation by silicon field-effect transistors", Applied Physics Letters, vol. 85, No. 4, Article 675, Jul. 23, 2004, pp. 675-677, doi: 10.1063/1.1775034.
Kocer et al., "A new transponder architecture with on-chip ADC for long-range telemetry applications", IEEE Journal of Solid-State Circuits, vol. 41, No. 5, May 2006, pp. 1142-1148, [online], [retrieved on Aug. 14, 2020]. Retrieved from the Internet <URL: https://www.mpflynngroup.com/uploads/7/3/4/9/73490609/01624404.pdf>,. (especially: fig. 1, p. 1, col. 2, para 3; p. 2, col. 2, para 2).
Kotani et al., "High-Efficiency Differential-Drive CMOS Rectifier for UHF RFIDs", IEEE Journal of Solid-State Circuits, vol. 44, No. 11, Nov. 2009, pp. 3011-3018, doi: 10.1109/JSSC.2009.2028955.
Kulkarni et al., "A 750 Mb/s, 12 pJ/b, 6-to-10 GHz CMOS IR-UWB Transmitter with Embedded On-Chip Antenna", IEEE Journal of Solid-State Circuits, vol. 44, No. 2, Feb. 2009, pp. 394-403, doi: 10.1109/JSSC.2008.2011034.
Kuo et al., "Near-field power transfer and backscattering communication to miniature RFID tag in 65 nm CMOS technology", 2016 IEEE MTT-S International Microwave Symposium (IMS), May 22-27, 2016, 4 pgs., doi: 10.1109/MWSYM.2016.7540221.
Kurs et al., "Wireless Power Transfer via Strongly Coupled Magnetic Resonances", Science, vol. 317, No. 5834, Jul. 6, 2007, published online Jun. 7, 2007, pp. 83-86, doi: 10.1126/science.1143254.
Le et al., "Efficient Far-Field Radio Frequency Energy Harvesting for Passively Powered Sensor Networks", IEEE Journal of Solid-State Circuits, vol. 43, No. 5, May 2008, pp. 1287-1302, doi: 10.1109/JSSC.2008.920318.
Lepock, "Cellular effects of hyperthermia: relevance to the minimum dose for thermal damage", International Journal of Hyperthermia, vol. 19, No. 3, May-Jun. 2003, pp. 252-266, doi: 10.1080/0265673031000065042.
Li et al., "A 13.56 MHz Wireless Power Transfer System With Reconfigurable Resonant Regulating Rectifier and Wireless Power Control for Implantable Medical Devices", IEEE Journal of Solid-State Circuits, vol. 50, No. 4, Apr. 1, 2015, pp. 978-989.
Li et al., "Parylene-based integrated wireless single-channel neurostimulator", Sensors and Actuators A: Physical, vol. 166, No. 2, Apr. 2011, pp. 193-200, doi: 10.1016/j.sna.2010.03.003.
Lisauskas et al., "Rational design of high-responsivity detectors of terahertz radiation based on distributed self-mixing in silicon field-effect transistors", Journal of Applied Physics, vol. 105, No. 11, Article 114511, Jun. 9, 2009, pp. 114511-1-114511-7, doi: 10.1063/1.3140611.
Liu et al., "A 10-bit 50-MS/s SAR ADC With a Monotonic Capacitor Switching Procedure", IEEE Journal of Solid-State Circuits, vol. 45, No. 4, Apr. 2010, pp. 731-740, doi: 10.1109/jssc.2010.2042254.
Liu et al., "A 650-pJ/bit MedRadio transmitter with an FIR-embedded phase modulator for medical micro-power networks (MMNs)", IEEE Transactions on Circuits and Systems I: Regular Papers, vol. 60, No. 12, 2013, pp. 3279-3288, doi: 10.1109/TCSI.2013.2265970.
Lo et al., "A fully integrated wireless SoC for motor function recovery after spinal cord injury", IEEE Transactions on Biomedical Circuits and Systems, vol. 11, No. 3, Jun. 2017, pp. 497-509, first published May 23, 2017, doi: 10.1109/TBCAS.2017.2679441.
Lo et al., "Bio-Impedance Characterization Technique with Implantable Neural Stimulator Using Biphasic Current Stimulus", Conference Proceedings of the IEEE Engineering in Medicine and Biology Society, 2014, pp. 474-477, doi: 10.1109/EMBC.2014.6943631.
Lonappan et al., "Nondestructive Measurement of Human Blood at Microwave Frequencies", Journal of Electromagnetic Waves and Applications, vol. 21, No. 8, 2007, pp. 1131-1139, doi: 10.1163/156939307781749740.

(56) References Cited

OTHER PUBLICATIONS

Lopez-Lapena et al., "A closed-loop maximum power point tracker for subwatt photovoltaic panels", IEEE Transactions on Industrial Electronics, vol. 59, No. 3, Mar. 2012, pp. 1588-1596, doi: 10.1109/TIE.2011.2161254.

Lu et al., "Flexible Neural Electrode Array Based-on Porous Graphene for Cortical Microstimulation and Sensing", Scientific Reports, vol. 6, No. 33526, Sep. 19, 2016, 9 pgs., doi: 10.1038/srep33526.

Lu et al., "Ultra-flexible Piezoelectric Devices Integrated with Heart to Harvest the Biomechanical Energy", Scientific Reports, vol. 5, No. 16065, Nov. 5, 2015, 9 pgs., doi: 10.1038/srep16065.

Lyu et al., "A 430-Mhz Wirelessly Powered Implantable Pulse Generator With Intensity/Rate Control and Sub-1 µA Quiescent Current Consumption", IEEE Transactions on Biomedical Circuits and Systems, vol. 13, No. 1, Feb. 2019, pp. 180-190, doi: 10.1109/TBCAS.2018.2879357.

Lyu et al., "A 915-MHz Far-Field Energy Harvester with −22-dBm Sensitivity and 3-V Output Voltage Based on Antenna-and-Rectified Codesign", IEEE Microwave and Wireless Components Letters, vol. 29, No. 8, Aug. 2019, pp. 557-559, doi: 10.1109/LMWC.2019.2923685.

Lyu et al., "A Multi-site Heart Pacing Study Using Wirelessly Powered Leadless Pacemakers", IEEE Xplore, Year: 2018, Date Uploaded: Oct. 28, 2018 (retrieved on Jan. 15, 2020), pp. 3434-3437.

Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, doi: 10.1109/TBCAS.2018.2852680.

Lyu et al., "Synchronized Biventricular Heart Pacing in a Closed-chest Porcine Model based on Wirelessly Powered Leadless Pacemakers", Scientific reports, vol. 10, No. 1, 2020, pp. 1-9, doi: 10.1038/s41598-020-59017-z.

Lyu et al., "Towards the Implementation of a Wirelessly Powered Dielectric Sensor with Digitized Output for Implantable Applications", IEEE Sensors Letters, vol. 3, No. 3, Mar. 2019, pp. 1-4, first published Jan. 30, 2019.

Mandal et al., "Low-power CMOS rectifier design for RFID applications", IEEE Transactions on Circuits and Systems I: Regular Papers, vol. 54, No. 6, Jul. 2007, pp. 1177-1188, doi: 10.1109/TCSI.2007.895229.

Meyer et al., "First in a series on the leadless pacing: Percutaneous implantable transcatheter pacemaker—background, technical aspects, and possible pitfalls", d-Journal of Cardiology Practice, vol. 14, No. 20, Aug. 23, 2016, 18 pgs.

Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, doi: 10.1109/TBCAS.2015.2466592.

Mirzavand et al., "High-Resolution Dielectric Sensor Based on Injection-Locked Oscillators", IEEE Sensors Journal, vol. 18, No. 1, Jan. 1, 2018, pp. 141-148, published online published Nov. 13, 2017, doi: 10.1109/JSEN.2017.2772923.

Montgomery et al., "Wirelessly powered, fully internal optogenetics for brain, spinal and peripheral circuits in mice", Nature Methods, vol. 12, No. 10, 2015, pp. 969-974, published online Aug. 17, 2015, doi: 10.31038/nmeth.3536.

Niemann et al., "Longevity of Implantable Pulse Generators in Bilateral Deep Brain Stimulation for Movement Disorders", Neuromodulation, vol. 21, No. 6, Aug. 2018, published online Dec. 19, 2017, pp. 597-603, doi: 10.1111/ner.12743.

Otsuji et al., "Terahertz Plasmonics: Good Results and Great Expectations", IEEE Microwave Magazine, vol. 15, No. 7, Nov.-Dec. 2014, pp. 43-50, DOI: 10.1109/MMM.2014.2355712.

Pandey et al., "A Sub-100 µW MICS/ISM Band Transmitter Based on Injection-Locking and Frequency Multiplication", IEEE Journal of Solid-State Circuits, vol. 46, No. 5, May 2011, pp. 1049-1058, first published Apr. 5, 2011, doi: 10.1109/JSSC.2011.2118030.

Papotto et al., "A 90nm CMOS 5mb/s crystal-less rf transceiver for rf-powered wsn nodes", 2012 IEEE International Solid-State Circuits Conference, Feb. 19-23, 2012, pp. 452-453, doi: 10.1109/ISSCC.2012.6177087.

Paul, "Inductance: loop and partial", John Wiley & Sons, 2011, 395 pgs.

Pedregosa et al., "Scikit-learn: Machine Learning in Python", Journal of Machine Learning Research, vol. 12, Oct. 2011, pp. 2825-2830.

Pellerano et al., "A mm-Wave Power-Harvesting RFID Tag in 90 nm CMOS", IEEE Journal of Solid-State Circuits, vol. 45, No. 8, Aug. 2010, pp. 1627-1637, doi: 10.1109/JSSC.2010.2049916.

Pozar, David M. "Microwave Engineering", John Wiley & Sons, Inc., Third Edition, 2005, Chapter 13 (Oscillators and Mixers): pp. 604-657, Chapter 14 (Introduction to Microwave Systems): pp. 658-708, 105 pgs.

Preu et al., "Terahertz Detection by a Homodyne Field Effect Transistor Multiplicative Mixer", IEEE Transactions on Terahertz Science and Technology, First Published: Apr. 24, 2012, vol. 2, No. 3, May 2012, pp. 278-283, doi: 10.1109/TTHZ.2012.2191671.

Radiom et al., "Far-Field On-Chip Antennas Monolithically Integrated in a Wireless-Powered 5.8-GHz Downlink/UWB Uplink RFID Tag in 0.18-µm Standard CMOS", IEEE Journal of Solid-State Circuits, vol. 45, No. 9, Sep. 2010, pp. 1746-1758, doi: 10.1109/JSSC.2010.2055630.

Rahmani et al., "A 1.6mm3 Wirelessly Powered Reconfigurable FDD Radio with On-Chip Antennas Achieving 4.7 pJ/b TX and 1 pJ/b RX Energy Efficiencies for Medical Implants", Conference: 2020 IEEE Custom Integrated Circuits Conference (CICC), Apr. 2020, 4 pgs., doi: 10.1109/CICC48029.2020.9075935.

Rahmani et al., "A Dual-Mode RF Power Harvesting System With an On-Chip Coil in 180-nm SOI CMOS for Millimeter-Sized Biomedical Implants", IEEE Transactions on Microwave Theory and Techniques, vol. 67, No. 1, Jan. 1, 2019, pp. 414-428, XP011695538, ISSN: 0018-9480, doi: 10.1109/TMTT.2018.2876239.

Becerra-Fajardo et al., "In Vivo Demonstration of Addressable Microstimulators Powered by Rectification of Epidermically Applied Currents for Miniaturized Neuroprostheses", PLoS One, vol. 10, No. 7, Article e0131666, Jul. 6, 2015, 19 pgs., doi: 10.1371/journal.pone.0131666.

* cited by examiner

CLOSED-LOOP WIRELESS STIMULATION SYSTEMS WITH WIRELESSLY POWERED STIMULATORS AND RECORDERS

CROSS REFERENCE TO RELATED APPLICATIONS

This application is a national stage of PCT Patent Application No. PCT/US2022/071066 entitled "Closed-loop Wireless Stimulation Systems with Wirelessly Powered Stimulators and Recorders" filed Mar. 10, 2022, which claims priority under 35 U.S.C. 119 (e) to U.S. Provisional Patent Application Ser. No. 63/159,219, entitled "Closed-loop Wireless Stimulation Systems with Wirelessly Powered Stimulators and Recorders", filed Mar. 10, 2021, the disclosures of which are incorporated herein by reference in their entirety.

FIELD OF THE INVENTION

The present invention generally relates to biomedical treatment systems with closed-loop implantable treatment devices for sensing bioelectrical signals and stimulating an implant site.

BACKGROUND

Biomedical implantable devices have solved various critical medical problems and improved the quality of human life. Their applications can include chronic pain relief, motor function recovery for spinal cord injuries, cardiac pacemaking, among various other applications. Conventional biomedical implantable devices can be bulky with the battery taking up most of the unit, and the necessary leads are prone to cause various complications.

SUMMARY OF THE INVENTION

System and methods for biomedical treatment systems with closed-loop implantable treatment devices are described. In an embodiment, an implantable treatment device, includes: an energy harvesting circuit configured to harvest ambient energy, where the ambient energy is at least one energy selected from the group consisting of ambient electrical, magnetic energy, and electromagnetic energy; a sensing circuit that senses bioelectrical signals and generates bioelectrical signal data; a stimulator circuit coupled to a set of electrodes to deliver a stimulation via at least one electrode from the set of electrodes based on a set of control signals received from an external controller that determine a set of parameters of the stimulation; and a communication circuit configured to (1) transmit to the external controller the bioelectrical signal data and (2) control the stimulator circuit to deliver energy via at least one electrode from the set of electrodes in response to the control signals received from the external controller.

In a further embodiment, the bioelectrical signal is at least one signal selected from the group consisting of a neural signal, a neural LFP (local field potential), an electrocardiogram (ECG) signal, a compound action potential, an electromyogram (EMG) signal, an Electroencephalogram (EEG) signal, an Electromyogram (EMG) signal, an Electrooculogram (EOG) signal, an Electroretinogram (ERG) signal, and an Electrogastrogram (EGG) signal.

In a further embodiment, the sensing circuit digitizes the bioelectrical signals to generate bioelectrical signal data.

In a further embodiment, the bioelectrical signal data are used to optimize a plurality of parameters of the stimulation delivered by the stimulator circuit.

In a further embodiment, the plurality of parameters includes at least one parameter selected from the group consisting of the stimulation pulse duration, amplitude of the stimulation, frequency of the stimulation, and directionality and phase response of the stimulation (mono phasic vs biphasic).

In a further embodiment, the external controller processes the bioelectrical signal data to generate the set of control signals.

In a further embodiment, the implantable treatment device is a closed loop neural stimulation system.

In a further embodiment, the energy harvesting circuit is wirelessly powered.

In a further embodiment, the bioelectrical signals are neural signal that range from 1 uV to 100 Mv In a further embodiment, the implantable treatment device further includes filter circuitry that filters the bioelectrical signals and digitizes the filtered bioelectrical signals.

In a further embodiment, the filter circuitry is designed to pass signals from 0.1 Hz to 10 KHz.

In a further embodiment, the filter circuitry passes more of a frequency content of the bioelectrical signal while removing out of band noise.

In a further embodiment, the bioelectrical signals are sensed within a preprogrammed time after a stimulation occurs.

In a further embodiment, the preprogrammed time sensing starts at a particular time after a stimulation occurs, where the particular time is a time selected from the group consisting of 1 usec, 10 usec, 100 usec, 1 msec, 10 msec, and 100 msec after the simulation occurs.

In a further embodiment, the sensing is done in an intermittent fashion with a duty cycle of less than 20%.

In a further embodiment, the stimulator circuit stimulates a body part in at least one body region selected from the group consisting of peripheral nerves, spinal cord, vagus nerve, central nervous system, sacral nerve, occipital nerve, hypoglossal nerve, kidney, bladder, brain, lung, heart, muscle, and fat.

In a further embodiment, the set of control signals provide several stimulation parameters for the stimulation that are optimized using processing performed in the cloud.

In a further embodiment, the control signals provide several stimulation parameters that are optimized for the stimulation using data from several different patients.

In a further embodiment, the control signals provide several stimulation parameters that are optimized for the stimulation with respect to a specific patient.

In a further embodiment, the energy harvesting circuit includes using energy stored within a rechargeable battery.

In a further embodiment, the energy harvesting circuit includes using energy from at least one capacitor.

In another embodiment, a treatment system, includes: an external controller; and a plurality of implantable treatment devices, each implantable treatment device configured for placement in, on, or adjacent an implant site, and comprising: a plurality of electrodes; a power harvesting circuit configured to receive energy from an external power source; a sensing circuit coupled to a sensing/recording set of the plurality of electrodes to sense bioelectrical signals and generate bioelectrical signal data; a stimulator circuit coupled to a stimulation set of the plurality of electrodes to deliver energy to the implant site; and a communication circuit coupled to the sensing circuit and the stimulator circuit and comprising a transmitter circuit configured to transmit to the external controller the sensed bioelectrical signal data, and a receiving circuit configured to receive stimulation control signals from the external controller and to control the stimulator circuit to deliver energy via the stimulation set of the plurality of electrodes according to stimulation control signals.

In a further embodiment, each implantable treatment device is configured for placement in, on, or adjacent an implant site corresponding to one of: a peripheral nerve, a spinal cord, a vagus nerve, a central nervous system, a sacral nerve, an occipital nerve, a hypoglossal nerve, a kidney, a bladder, a brain, a lung, a heart, a muscle, and fat.

In a further embodiment, the external controller includes: a bioelectrical data processing engine configured to process bioelectrical signal data received from at least one implantable treatment device; and a stimulation control data generator configured to generate stimulation control signals for at least one implantable treatment device based on the bioelectrical signal data.

In a further embodiment, the external controller further includes: a data transceiver configured to transmit the stimulation control signals to at least one implantable treatment device.

In a further embodiment, the external controller further includes: a power delivery circuit configured to deliver power to the plurality of implantable treatment devices.

In a further embodiment, the stimulation set of electrodes and the sensing/recording set of electrodes are spaced apart; and the sensing circuit is configured to: estimate a time window where a stimulation signal delivered by the stimulation set of electrodes arrives at the sensing/recoding set of electrodes, determine a time based on the estimated time window, and sense and record bioelectrical signals via the sensing/recording set of electrodes according to the determined time.

In a further embodiment, the determined time comprises one of 1 usec, 10 usec, 100 usec, 1 msec, 10 msec, and 100 msec.

In a further embodiment, the stimulation set of electrodes and the sensing/recording set of electrodes are spaced apart; and the sensing circuit is configured to: estimate a speed of the transfer of an activated neural signal from the location of the stimulation set of electrodes to the location of the sensing/recoding set of electrodes, determine a time based on the estimated speed, and sense and record bioelectrical signals via the sensing/recording set of electrodes according to the determined time.

In a further embodiment, the sensing circuit is configured to measure an evoked compound action potential (ECAP) based on bioelectrical signals sensed at the sensing/recording set of electrodes; the communication circuit is configured to transmit the measure of ECAP to the external controller; and the external controller is configured to adjust one or more stimulation parameters based on the ECAP, to maintain an appropriate level of neural activity.

In another embodiment, a method of therapy delivery by a treatment system, the method includes: sensing, through at least one implantable treatment device placed at an implant site, bioelectrical activity at the implant site; transmitting, through the at least one implantable treatment device, bioelectrical data corresponding to sensed bioelectrical activity to an external controller; receiving, through at least one implantable treatment device placed at an implant site, stimulation control data derived at least in part from the bioelectrical data by the external controller; and delivering, through the at least one implantable treatment device, a stimulation based on the stimulation control data.

In a further embodiment, the at least one implantable treatment device includes a stimulation set of electrodes spaced apart from a sensing/recording set of electrodes, and the method further comprising: estimating a time window where a stimulation signal delivered by the stimulation set of electrodes arrives at the sensing/recoding set of electrodes, determining a time based on the estimated time window, and sensing/recording bioelectrical signals via the sensing/recording set of electrodes according to the determined time.

In a further embodiment, the at least one implantable treatment device includes a stimulation set of electrodes spaced apart from a sensing/recording set of electrodes, and the method further comprising: estimating a speed of the transfer of an activated neural signal from the location of stimulation set of electrodes to the location of the sensing/recoding set of electrodes, determining a time based on the estimated speed, and sensing/recording bioelectrical signals via the sensing/recording set of electrodes according to the determined time.

In a further embodiment, the at least one implantable treatment device includes a stimulation set of electrodes spaced apart from a sensing/recording set of electrodes, and the method further comprising: measuring an evoked compound action potential (ECAP) based on bioelectrical signals sensed at the sensing/recording set of electrodes; transmitting the measure of ECAP to the external controller; and adjusting one or more stimulation parameters based on the ECAP, to maintain an appropriate level of neural activity.

In another embodiment includes an external treatment device configured for placement on a body part adjacent a treatment site, and including: a plurality of electrodes, a stimulator circuit coupled to the electrodes, and a receiving circuit configured to wirelessly receive stimulation control signals and to control the stimulator circuit to deliver energy via the plurality of electrodes according to stimulation control signals; at least one implantable treatment device configured for placement in, on, or adjacent a treatment site, and includes: a plurality of electrodes; an power harvesting circuit configured to receive energy from an external power source; a sensing circuit coupled to a sensing set of the plurality of electrodes to sense bioelectrical signals and generate bioelectrical signal data; and a communication circuit coupled to the sensing circuit and comprising a transmitter circuit configured to transmit the sensed bioelectrical signal data; and an external controller configured to receive the sensed bioelectrical signal data from the at least one implantable treatment device, and to transmit stimulation control signals to the external treatment device.

In a further embodiment, the external treatment device includes a sleeve configured to wrap around a patient's arm.

DETAILED DESCRIPTION OF THE DRAWINGS

Figure 1A:
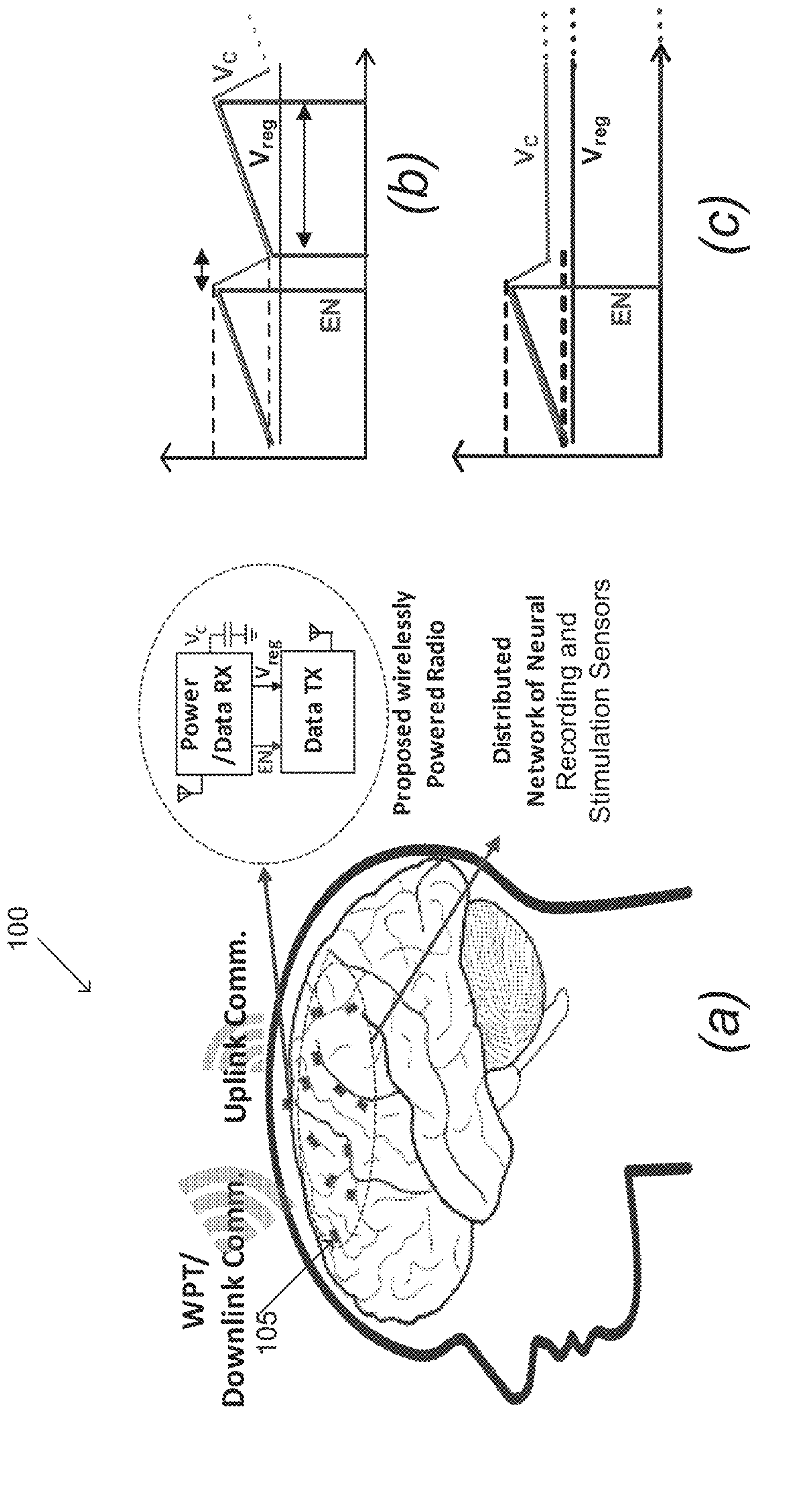
FIG. 1A illustrates a closed-loop treatment system with one or more implantable treatment devices for neural recording and stimulation in accordance with an embodiment of the invention.

Turning now to the drawings, closed-loop treatment systems for recording and stimulation in accordance with various embodiments of the invention are illustrated. Further details of the closed-loop recording and stimulation systems are discussed in U.S. Provisional Patent Application 63/127,702 entitled "Wireless Recording System-on-chip for Distributed Neural Interface Systems with Inductive Power Delivery and UWB Data Transmission" by Rahmani et al., and U.S. PCT Application PCT/US2021/020343 entitled "Integrated Energy Harvesting Transceivers and Transmitters With Dual-Antenna Architecture for Miniaturized Implants and Electrochemical Sensors" by The Regents of the University of California et al., and U.S. PCT Application Number PCT/US2020/048001 entitled "Wirelessly Powered Stimulator", by The Regents of the University of California et al., the entirety of which are herein incorporated by reference.

Emerging applications of Brain Machine Interface (BMI) systems show an ever-increasing demand for neural activity acquisition with higher data-rates and better spatiotemporal resolutions. Accordingly, many embodiments provide for a treatment system that includes an external controller wirelessly communicating with at least one implantable treatment device implantable in a location with respect to a body part, including on, within and/or proximate a tissue. In many embodiments the implantable treatment device can be a brain implant that is implanted to sense and record neural activity and stimulate electrodes on the brain and/or electrodes on different body parts. In certain embodiments, the treatment system including the one or more implantable treatment device can be for any of a variety of biomedical implant applications, including pace makers, brain implants, spinal cord implants, among various other applications.

In many embodiments, the treatment system can include an external controller that wirelessly communicate and/or provides wireless power to one or more implantable treatment devices. In certain embodiments, the external controller can include a rechargeable battery that provides power and/or communicates thru wiring to one or more implantable treatment devices. In several embodiments, the external controller can be a wearable device worn on a body part of a patient. In certain embodiments, the external controller can be a software application executing on a computer, smartphone application, among other types of devices, and/or one or more cloud servers.

In many embodiments, the treatment system can include an external controller communicating with an array of implantable treatment devices, where each implantable treatment device includes a semiconductor substrate that includes a communication circuit, an energy harvesting circuit, and a stimulation delivery circuit. In many embodiments, an array of wirelessly powered implantable treatment devices can be placed at different spatial locations on a body part (e.g., brain, heart, among various others) and each implantable treatment device can sense and/or stimulate a specific location, and wirelessly communicate with a centralized external controller in order to provide the controller with the sensed activity and to receive control signals from the external controller regarding various stimulation parameters. Accordingly, unlike many prior art brain implants and heart implants that placed electrodes within a confined spatial location that required wiring between a controller and the recording/stimulation sites, many embodiments are able to place the recording and stimulation sites at any location on a body part without wiring.

In many embodiments, an implantable treatment device can include several circuits including an energy harvesting circuit, a stimulation delivery circuit and a communication circuit. In many embodiments, the energy harvesting circuit can be configured to harvest ambient energy, where the ambient energy can be ambient electrical, magnetic energy, and/or electromagnetic energy. The implantable treatment device can include a stimulation delivery circuit coupled to a set of electrodes to deliver energy to an implant site, and a communication circuit configured to control the stimulation delivery circuit to deliver energy via at least one electrode from a set of electrodes. In many embodiments, the stimulation delivery circuit can deliver energy via the electrodes in response to wireless control signals received from an external controller, where the control signals provide a variety of different parameters of the stimulation. In particular, in many embodiments, the implantable treatment device can wirelessly transmit sensed and recorded bioelectrical signals (e.g., neural signals from a brain, bioelectrical signals from a heart, among other types of bioelectrical signals obtained from different body parts) activity to an external controller and the external controller can process the recorded bioelectrical activity and transmit an optimized set of stimulation control signals to the implantable treatment device to stimulate an implant site based on the sensed bioelectrical signal activity. The bioelectrical signals may also be referred to and discussed herein as neural signals, neural LFP (local field potential), an electrocardiogram (ECG) signal, compound action potential, an electromyogram (EMG) signal, an Electroencephalogram (EEG) signal, an Electromyogram (EMG) signal, an Electrooculogram (EOG) signal, an Electroretinogram (ERG) signal, and/or an Electrogastrogram (EGG) signal, among various other types of bioelectrical signals.

In many embodiments, the implantable treatment device can be wirelessly powered to sense and record bioelectrical (e.g., neural, cardiac, among various others) activities. The sensing can be done before, during, and/or after stimulation. The implantable treatment device can digitize a bioelectrical signal prior to processing the bioelectrical signal. The digitized bioelectrical (e.g., neural, cardiac, etc.) signal can be processed in the implantable treatment device. In certain embodiments, the implantable treatment device can include a wirelessly powered transmitter, where a digitized signal is transmitted wirelessly to an external controller using the wirelessly powered transmitter. A sensed bioelectrical signal and bioelectrical activity can be used to optimize a plurality of parameters of the stimulation delivery circuit of the implantable treatment device. In many prior art applications, the placement of a stimulation contact can be wrong, or the quality of the contact is low. In some prior art devices, more than one electrode has been used to increase the redundancy and improve the results. However, redundancy can fail and thus is not sufficient in many applications. To address this issue, many embodiments are able to demonstrate that a stimulation is happening, and that neurons get activated. Accordingly, many embodiments use a sensing/recording node to measure the quality of a stimulation. Many embodiments are able to achieve this by placing a sensing/recording node at a set distance from a stimulation node. In embodiments where sensing/recording and stimulation are enabled through electrodes, a sensing/recording node may be defined by a first set electrodes and a stimulation node may be defined by a second set of electrodes. By estimating the speed of the transfer of the neural signal in the body, many embodiments are able to estimate a time window where the stimulation signal arrives at the sensing/recoding node. This can help to verify that neurons are activated and also verify that the activation of the neurons are due to the stimulation waveform. Accordingly, an implantable treatment device can sense and measure the evoked compound action potentials (ECAPs) and then an external controller can automatically adjust one or more stimulation parameters, including the stimulation amplitude (e.g., current or voltage) to maintain an appropriate level of neural activity. In many embodiments, the sensing can help to optimize a dose of the stimulation and also identify the quality of the contact with the tissue and the neurons.

In certain embodiments, the SNR measured at a sensing/recoding node may not be sufficient. To address this issue, many embodiments may repeat the stimulation and re-measure the neural activity at a sensing/recording node and use averaging of the sensed/recorded signals to improve SNR.

In many embodiments, the treatment system can optimize a set of power delivery and power consumption parameters based on characteristics of an implantable treatment device at a particular implant location. For example, the treatment system can minimize and/or optimize the power consumption settings of an implantable treatment device based on detected characteristics of the operation of the implantable treatment device at a particular implant site. For example, for an implantable treatment device implanted deep within a tissue, the implantable treatment device may consume more power to send wireless data to the external controller than an implantable treatment device located near the surface of a tissue. Accordingly, the treatment system can detect, based on measured characteristics of the bioelectrical sensing data and stimulation data, an optimal set of power consumption settings and stimulation parameters for a particular implantable treatment device at a particular implant location using real-time operation data of the implantable treatment device.

In many embodiments, the bioelectrical activity from different implantable treatment devices in a particular patient can be used to determine one or more parameters for a particular treatment device in the patient. The parameters can include parameters for the stimulation delivery circuit of an implantable treatment device, including a stimulation pulse duration, amplitude of a stimulation, frequency of a stimulation, and directionality and phase response of a stimulation (e.g., mono phasic vs biphasic), among various other stimulation parameters. The external controller can process the bioelectrical signals recorded by the implantable treatment device to provide the control signals. The control signals can determine the stimulation parameters of the implantable treatment device, including the particular set of one or more implantable treatment devices and/or electrodes on the body that should be stimulated. In several embodiments, the implantable treatment device is a closed loop neural stimulation system. In many embodiments, the stimulation delivery circuit, energy sensing circuit, and/or an array of implantable treatment devices that sense and record bioelectrical activity and/or stimulate a tissue can be wirelessly powered. In many embodiments, the recorded neural signal can range from 1 uV to 100 mV. The recorded signal can be filtered before being digitized.

In many embodiments, the filter can be designed to pass signals from 0.1 Hz to 10 KHz. Accordingly, the filter may pass more of a frequency content of the neural signal while removing out of band noise.

In order to improve the quality of the recorded bioelectrical signals, many embodiments may time a stimulation according to the sensed neural activity. In particular, the neural signals may be sensed within a preprogrammed time after a stimulation occurs. This time can be determined by estimating the speed of the transfer of the activated neural signal from the location of the stimulation to the location of the sensing/recoding node.

In several embodiments, the preprogrammed time sensing starts at a particular time after a stimulation occurs, where the particular time can be at 1 usec, 10 usec, 100 usec, 1 msec, 10 msec, or 100 msec after the simulation occurs. In certain embodiments, the sensing can be done in an intermittent fashion with a duty cycle of less than a certain percentage. In certain embodiments, the duty cycle can be less than 20%. For example, sensing can be performed for 200 msec every 1 sec.

Many embodiments of the treatment system utilize energy harvesting and thus operate using a duty-cycling approach. The implantable treatment devices may turn on only for a certain percentage of the time (e.g., 1-10% of the time). For example, a recording or stimulation node may harvest 1 uW of average power and use it for only 1% of the time. This duty-cycling approach may allow the recording or stimulation nodes to boost the effect power by the inverse of the duty cycle. A recording and/or stimulation node can consume a certain amount of power for a certain period of time. For example, a recording and/or stimulation node can consume 100 uW DC power only for 1% of the time, while harvesting only 1 uW on average. Further details of the duty-cycling approach for both sensing and stimulation nodes are discussed in details in U.S. Provisional Patent Application 63/127,702 entitled "Wireless Recording System-on-chip for Distributed Neural Interface Systems with Inductive Power Delivery and UWB Data Transmission" by Rahmani et al., and U.S. PCT Application PCT/US2021/020343 entitled "Integrated Energy Harvesting Transceivers and Transmitters With Dual-Antenna Architecture for Miniaturized Implants and Electrochemical Sensors" by The Regents of the University of California et al., and U.S. PCT Application Number PCT/US2020/048001 entitled "Wirelessly Powered Stimulator", by The Regents of the University of California et al., the entireties of which are herein incorporated by reference.

In many embodiments, the implantable treatment device can be implanted in various different locations in a body without the need for intrusive wiring and bulky components. In particular, an array of implantable treatment devices can be positioned at any of a variety of locations and can each communicate with a centralized external controller to transmit recorded bioelectrical signals and to receive control signals regarding the stimulation parameters for stimulating a particular body part. The stimulation delivery circuit of an implantable treatment device can stimulate a body part that can include peripheral nerves, spinal cord, vagus nerve, central nervous system, sacral nerve, occipital nerve, hypoglossal nerve, kidney, bladder, brain, lung, heart muscle, and fat. In many embodiments, the stimulation and sensing in a particular body part can be used to optimize a plurality of stimulation parameters. In many embodiments, a first implanted treatment device located at a particular body part can sense and record signals and transmit the signals to the external controller. The external controller can process this and/or other signals from other implantable treatment devices, and transmit control signals to a second implantable treatment device located at a different location to stimulate a body part. Accordingly, different implantable treatment devices can sense and send signals to a centralized external controller that can process the various bioelectrical signals and determine optimization parameters for one or more different implantable treatment devices that can stimulate different locations of a body. In many embodiments, the external controller can use data from a particular patient to determine the optimization for the control signals. In several embodiments, the external controller can use data from different patients to determine the control signals. In particular, recorded bioelectrical signals (e.g., neural signals) can be processed using different patient data in order to determine the optimization stimulation parameters of a particular patients. In many embodiments, the external processing and optimizations can be done on the cloud, where information can be combined from multiple patients and one or more servers can perform the optimization. In certain embodiments, the optimization can be patient specific and the processes can be tailored to specific patient data.

Figure 1B:
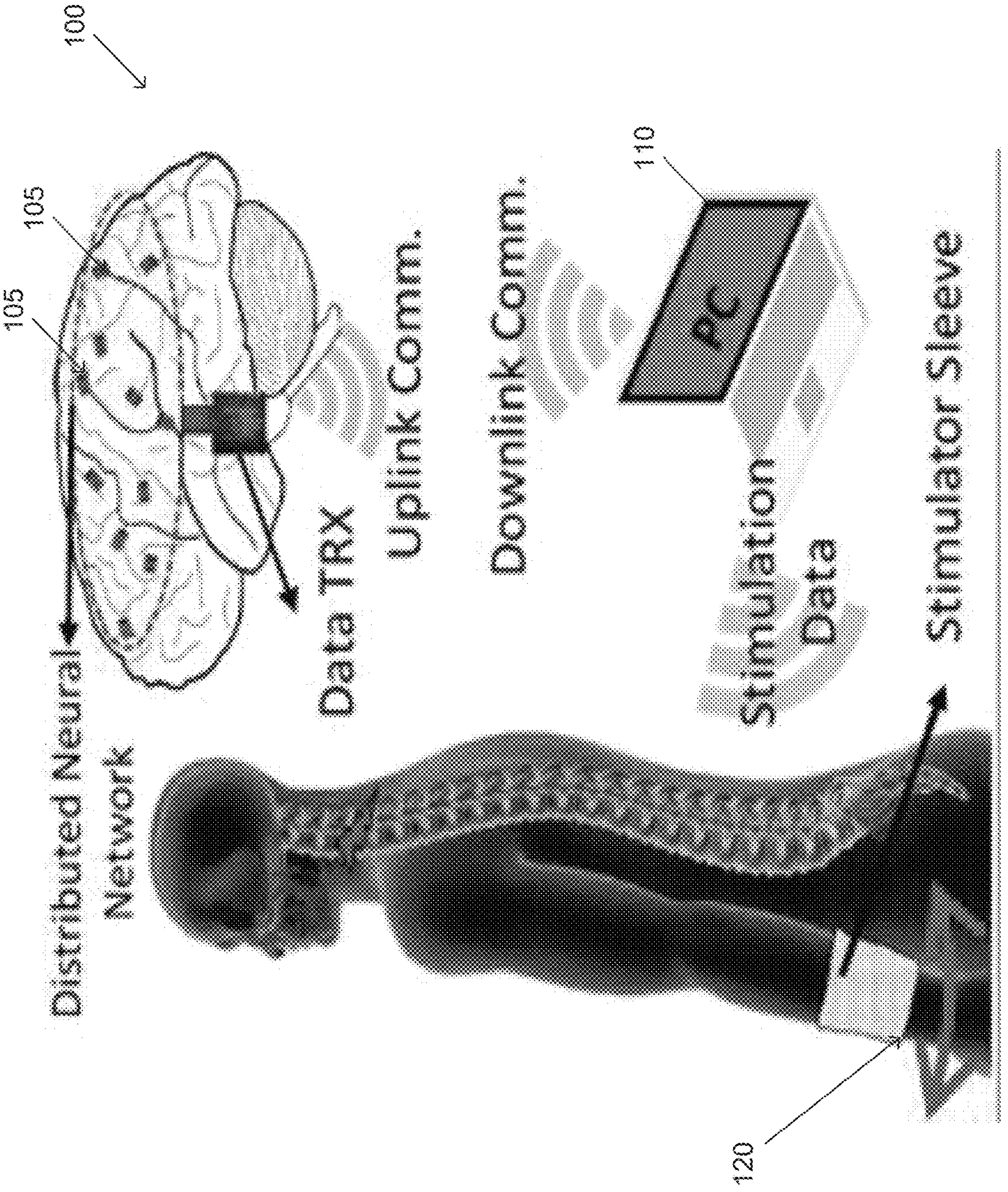
FIG. 1B illustrates a closed-loop treatment system with one or more implantable treatment devices for neural recording and stimulation system in accordance with an embodiment of the invention.

A closed-loop treatment system 100 with several implantable treatment devices 105 for neural recording and stimulation in accordance with an embodiment of the invention is illustrated in FIG. 1A and FIG. 1B. Neural signals (e.g., brain signals) can be sensed and recorded and nerves can be stimulated by a treatment system 100 that includes several implantable treatment devices 105 distributed at different locations on a body part and the data may be transmitted to an external processor 110 wirelessly. As illustrated, the treatment system can be used for neural sensing an stimulation and may comprise an array of implantable treatment devices 105 positioned at different locations on the brain, wherein each implantable treatment device 105 can be wirelessly powered, wirelessly sense and transmit bioelectrical (e.g., neural) signals to an external controller 110, and wirelessly receive control signals from the external controller 110 to determine a set of optimal stimulation parameters for the implantable treatment device and to stimulate one or more electrodes implanted on the brain. An implantable treatment device can include a semiconductor substrate that includes a communication circuit, an energy harvesting circuit, a stimulation delivery circuit, and/or a sensing circuit. After the neural signals are decoded, different body parts can be stimulated by electrodes, as illustrated in FIG. 1B, arm muscles can be stimulated by an electronic sleeve 120 wrapped around a patient's arm in order to help the patient regain control over their hand movement. Providing a real-time hand control thru stimulation is made possible in that many embodiments are able to acquire neural activity with a high throughput at a fine scale.

In a treatment system with a distributed network of implantable sensor devices for sensing and stimulation as illustrated in FIGS. 1A and 1B, miniaturizing the individual implantable treatment devices 105 can be an effective solution that renders more recording and stimulation sites and improves the resolution. Accordingly, many embodiments provide for a treatment system with a distributed network of implantable treatment devices based on a fully integrated system-on-chip (SoC). Further discussion of circuit designs that may be utilized for implantable treatment devices for neural recording and stimulation are described in U.S. Provisional Patent Application 63/127,702 entitled "Wireless Recording System-on-chip for Distributed Neural Interface Systems with Inductive Power Delivery and UWB Data Transmission" by Rahmani et al., and U.S. PCT Application PCT/US2021/020343 entitled "Integrated Energy Harvesting Transceivers and Transmitters With Dual-Antenna Architecture for Miniaturized Implants and Electrochemical Sensors" by The Regents of the University of California et al., and U.S. PCT Application Number PCT/US2020/048001 entitled "Wirelessly Powered Stimulator", by The Regents of the University of California et al., the entireties of which are herein incorporated by reference.

In many embodiments, the treatment system is able to improve the spatiotemporal resolution of the recorded bioelectrical signals to provide more insight into the complex mechanism of human functions. To enable recording and/or sensing at a fine scale, many embodiments of the invention utilize implantable System-on-Chips (SoCs) to realize a distributed treatment system for neural recording. The system-level requirements of such SoCs are long-term wireless operation, mm-sized form-factor, and integration capability on a commercial CMOS process to make them scalable and cost-efficient. Miniaturizing the size of an implantable treatment device can be a key step for fulfilling the needs of next-generation biomedical treatment systems with implantable treatment devices since it results in a higher sensor density and also enables signal recording at an ultra-small structural scale. FIG. 1A illustrates a conceptual multi-site and distributed treatment system 100 enabled by an array of mm-sized implantable treatment devices 105 for recording and/or stimulation in accordance with an embodiment of the invention. Each implantable treatment device 105 can include a data transceiver (TRX) that is placed on top of a microelectrode array. Due to the compact size, individual treatment devices 105 can be tightly placed on the brain or other tissues and thus improve the recording resolution.

There can be many challenges toward realizing a practical neural interface system. In many embodiments, each TRX can act as a communication hub between the electrodes within an implantable treatment device 105 and an external reader 110.

Many embodiments of the treatment system described here present the design, implementation, and verification of a fully integrated and RF-powered wireless implantable treatment device. The implantable treatment device can be implemented on a single CMOS silicon chip and include the various components for power delivery, energy storage, bioelectrical sensing, stimulation, and data communication, including an on-chip coil and a dipole antenna, can be implemented on the same chip. In certain embodiments, some components such as antennas can be located off chip.

Although specific implementations for closed-loop wireless treatment system with wirelessly powered implantable treatment devices for recording and stimulation are discussed above with respect to FIG. 1A and FIG. 1B, any of a variety of implementations utilizing the above discussed techniques can be utilized as appropriate to the requirements of specific applications in accordance with embodiments of the invention.

Figure 1C:
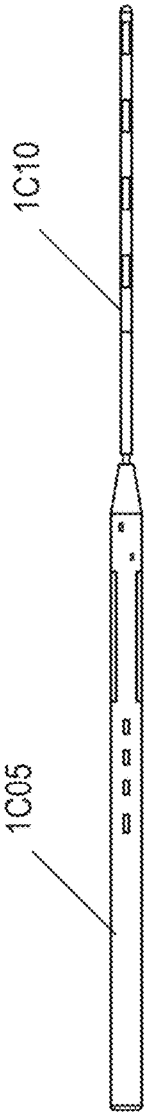
FIG. 1C illustrates an implantable treatment device in accordance with an embodiment of the invention.
Figure 1D:
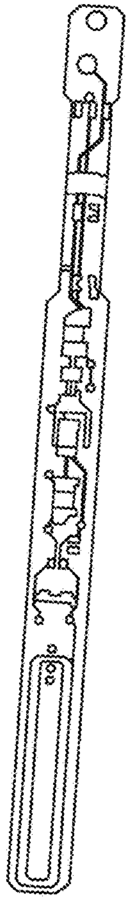
FIG. 1D illustrates a printed circuit board (PCB) of an implantable treatment device that includes a neurostimulation microchip and a recording microchip in accordance with an embodiment of the invention.
Figure 1E:
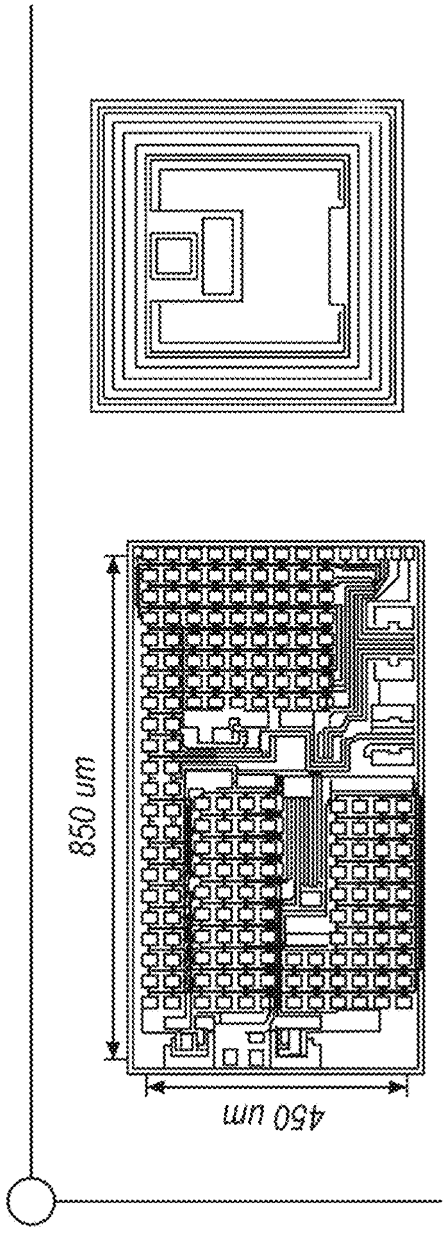
FIG. 1E illustrates an implantable treatment device with a neurostimulation microchip and a recording microchip in accordance with an embodiment of the invention.

FIG. 1C illustrates an implantable treatment device in accordance with an embodiment of the invention. As illustrated, the implantable treatment device can be a neurostimulator. The implantable treatment device can include a housing 1C05 connected to an electrode 1C10. Within the housing 1C05 can be a printed circuit board that includes a variety of microchips and circuitry. FIG. 1D illustrates a PCB of an implantable treatment device that includes a neurostimulation microchip, a recording microchip, and various other circuitry. FIG. 1E illustrates a neurostimulation microchip and a recording microchip in accordance with an embodiment of the invention. Although FIG. 1C-1E illustrate a particular implantable treatment device for neurostimulation and recording, any of a variety of implantable treatment device architectures can be utilized as appropriate to the requirements of specific applications, including applications to different body parts and types of bioelectrical activity in accordance with embodiments of the invention.

Treatment System Architecture

Figure 2A:
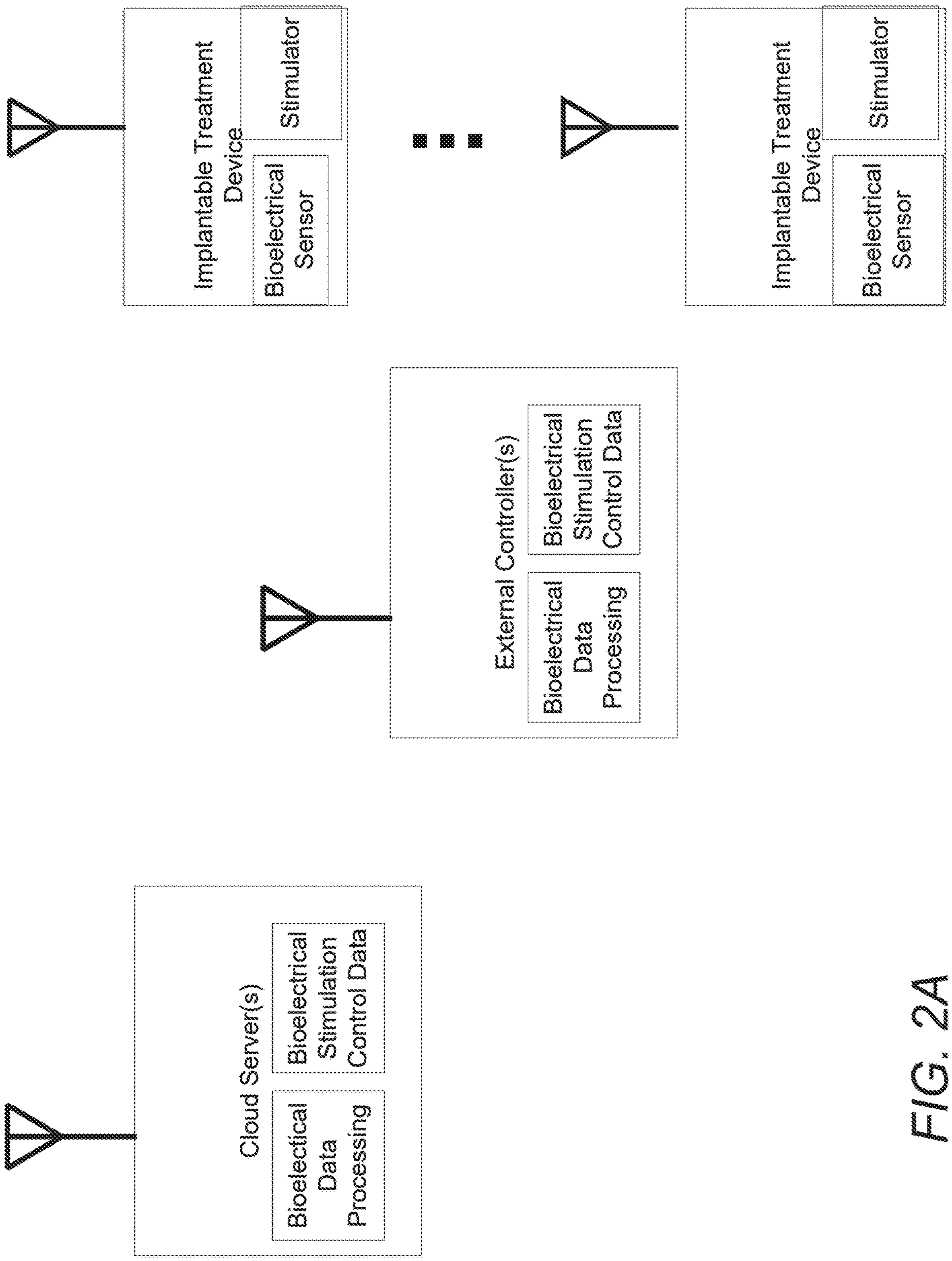
FIG. 2A illustrates a treatment system that includes an external controller, several implantable treatment devices, and one or more cloud servers in accordance with an embodiment of the invention.

A system architecture diagram of a treatment system in accordance with several embodiments of the invention is depicted in FIG. 2A. The treatment system can include one or more cloud servers, one or more external controllers, and one or more implantable treatment devices. Each of the implantable treatment devices can be implanted at different body part locations within a patient. An implantable treatment device can include a bioelectrical sensor and/or recorder than can sense and/or record bioelectrical signal activity and transmit the bioelectrical data to the external controller. An implantable treatment device can include a stimulator circuit than can deliver an energy to stimulate an implant location. In many embodiments, the implantable treatment device can wirelessly communicate with the external controller. In many embodiments, the implantable treatment device can be wirelessly powered. The wireless power can be received from the external controller. In certain embodiments, the implantable treatment device can be wired to receive power and/or communicate with the external controller. In certain embodiments, the implantable treatment devices and/or external controller can include rechargeable batteries that can be charged wirelessly and/or through wiring.

The external controller can receive bioelectrical signal data from one or more implantable treatment devices and can process the bioelectrical signal data. In many embodiment, the external controller can process the bioelectrical signal data to determine an optimal set of stimulation parameters for performing a stimulation by a particular implantable treatment device. The external controller can transmit the bioelectrical control data to one or more implantable treatment devices and the implantable treatment device can stimulate an implant location accordingly. The external controller can also communicate with one or more cloud servers, and the cloud servers can also process the bioelectrical data and/or generate optimized bioelectrical stimulation control data. Accordingly, many embodiments of the treatment system are able to minimize the power consumption of the implantable treatment devices by performing the more extensive power consuming processing of the bioelectrical signal data on the external controller and/or the cloud servers. Accordingly, the implantable treatment devices can minimize the power necessary to enable their operations.

Figure 2B:
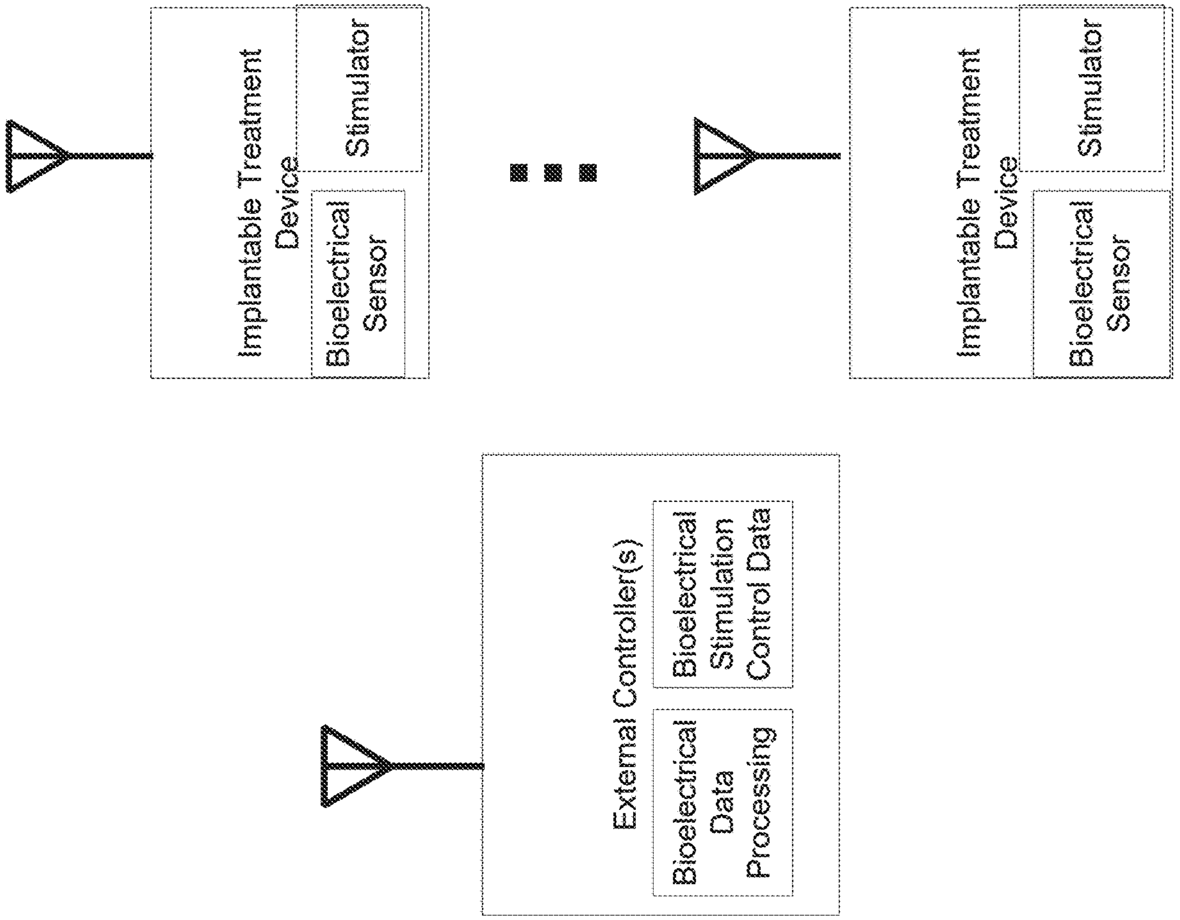
FIG. 2B illustrates a treatment system that includes an external controller and several implantable treatment devices in accordance with an embodiment of the invention.

FIG. 2B illustrates a treatment system that includes an external controller and several implantable treatment devices in accordance with an embodiment of the invention. Although FIG. 2A and FIG. 2B illustrate specific system architectures of treatment systems for recording bioelectrical data and stimulation of an implant site, any of a variety of architectures can be utilized as appropriate to the requirements of specific applications in accordance with embodiments of the invention.

Implantable Treatment Device System Architecture

Figure 3:
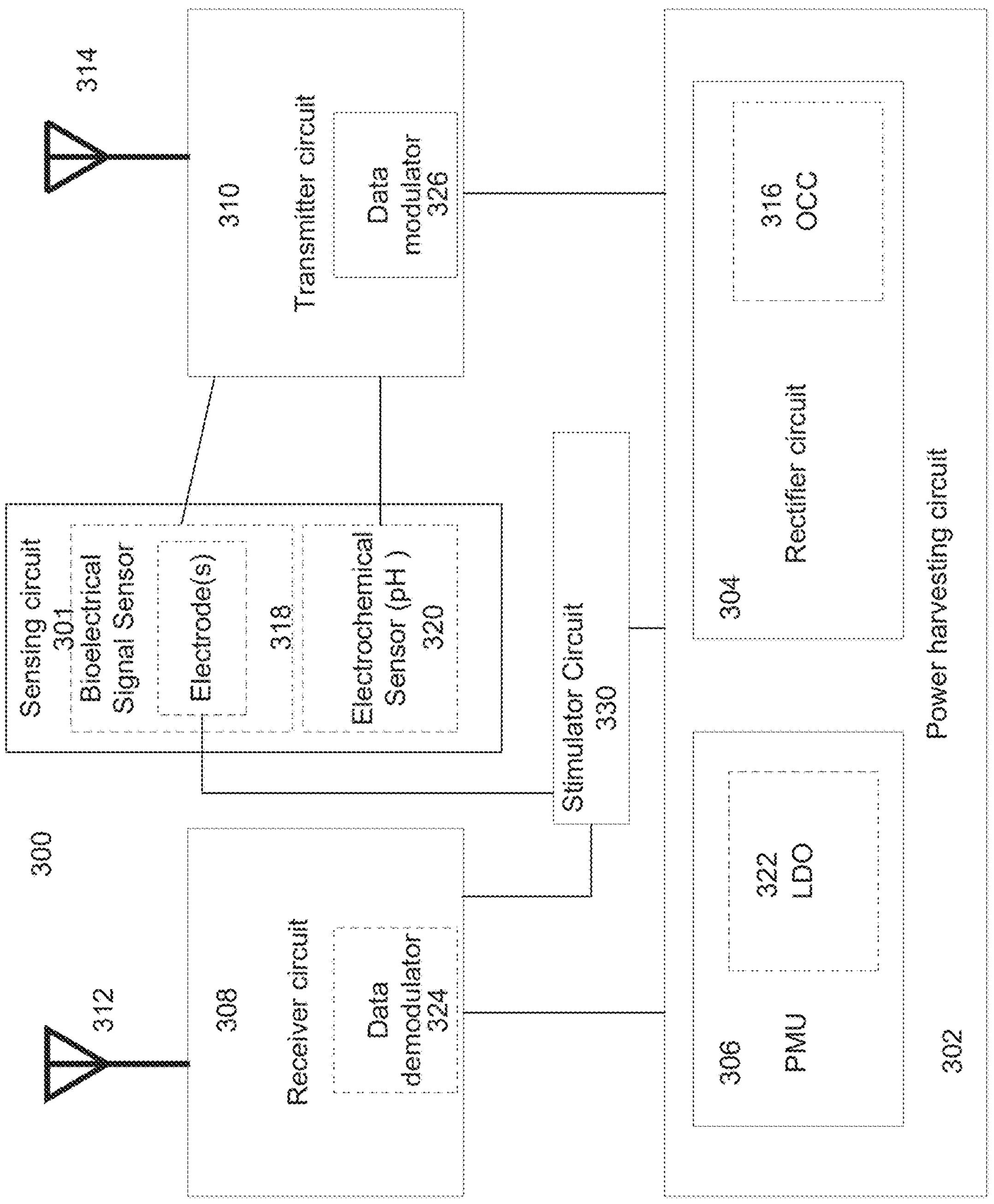
FIG. 3 illustrates a system architecture of an implantable treatment device for bioelectrical recording and stimulation in accordance with an embodiment of the invention.

A block diagram of an implantable treatment device in accordance with several embodiments of the invention is depicted in FIG. 3. The implantable treatment device 300 can include a power harvesting system 302, which includes a rectenna (rectifier circuit) 304 and a power management unit (PMU) 306, a receiver circuit (RX) 308, and a transmitter circuit (TX) 310. A receive antenna 312 is connected to the receiver circuit 308 and a transmit antenna 314 is connected to the transmitter circuit 310.

The rectenna 304, which may include an on-chip coil (OCC) 316, several full-wave rectifiers and a matching capacitor, can receive energy through an inductive link and convert RF energy into a DC voltage. The OCC can be shared between the power harvesting system 302 (for power) and the receiver 308 (for receiving data). The converted power by the rectenna can be used to power other components of the implantable treatment device 300 such as the data transmitter.

The receiver circuit 308 may include a data demodulator 324 to receiver data at the implantable treatment device. Some embodiments may not receive data and therefore may not have a data decoder in the receive circuit. Some embodiments may extract a clock signal from the received signal. In some embodiments, the receive antenna 312 is a loop antenna with a capacitor to utilize resonance inductive coupling. In other embodiments, the receive antenna 312 is a dipole antenna and other configurations maybe contemplated.

In several embodiments, the transmitter 310 includes a reconfigurable data modulator circuit 326 to send data out from the implantable treatment device. In different embodiments of the invention, the transmit antenna 314 can be a monopole, dipole, or loop antenna as appropriate to a particular application, although isolation from the receive antenna 312 is desirable.

The main power-consuming block of the implantable treatment device can be often the transmitter (TX) 310. Due to the challenges of power transfer to mm-sized implants, harvested power is often less than the instantaneous power consumption of the TX block 310. Therefore, power management unit (PMU) 306 can duty-cycle the operation of the data TX 310 to maintain a minimum voltage across the storage capacitor ($C_S$) and establish charging and discharging modes for $C_S$. In charging mode, the converted power by the rectenna increases the voltage level across $C_S$ ($V_C$) until the PMU 306 activates the TX block 310. PMU 306 and data receiver (RX) 308 blocks can be active during the entire operation and constituent sub-circuits are designed in subthreshold region to maximize sensitivity and reduce the charging time ($t_{charge}$) of $C_S$. On the other hand, discharging time ($t_{discharge}$) of $C_S$ is proportional to the capacitance value; hence using a large capacitance enables the PMU to follow rapid transitions of $V_C$. In several embodiments of the invention, in order to achieve a high capacitance density, MIM capacitors (2 fF/μm2) are stacked over MOSCAP devices (5.5 fF/μm2) to realize a 5 nF capacitor, although other designs may be utilized to achieve a target capacitance. The transition from charging mode to discharging mode represents a significant load variation for the low dropout voltage regulator (LDO) 322 in the PMU 306. To ensure the regulator remains functional, the bandwidth of the error amplifier can be increased at the onset of active mode. The PMU 306 can adaptively change the bias condition of the LDO and enables it to maintain a constant voltage at its output.

In several embodiments of the treatment system, an implantable treatment device for a bioelectrical recording and stimulation application (e.g., neural recording and stimulation) based on sensed bioelectrical activity can receive information from a sensing circuit 301 that includes a bioelectrical signal sensor 318 that includes a set of sensing/recording electrodes and stimulate a body part (e.g., nerve, tissue, among various other body parts) using stimulator circuit 330 (e.g., an energy delivery circuit) connected to a set of stimulating electrodes. A bioelectrical signal sensor 318 can include any of a variety of sensors, configured to capture electrical signals from which one or more of the following can be derive: neural LFP (local field potential), an electrocardiogram (ECG) signal, compound action potential, an electromyogram (EMG) signal, an Electroencephalogram (EEG) signal, an Electromyogram (EMG) signal, an Electrooculogram (EOG) signal, an Electroretinogram (ERG) signal, and/or an Electrogastrogram (EGG) signal. Such sensors sense electrical signals, potential, or other characteristics in a variety of ways such as the difference between two electrodes, electrical resistance, or the magnetic field induced by electrical currents. Such sensing applications may complement neural stimulation for a variety of therapies, such as pain control.

In some other embodiments of the invention, a transmitter for electrochemical sensing can include an electrochemical sensor 320, such as a pH sensor. Such sensors may be used in industrial or environmental applications.

In many embodiments, a 250 MHz signal is utilized to power the implantable treatment device by received signal as it provides high penetration, and higher harmonics of this frequency can cause interference. Additionally, the received power signal may utilize amplitude modulation. In several embodiments, a 4.15 GHz center frequency is utilized for the transmit signal to provide high bandwidth and avoid harmonics of the receiver frequency. Frequencies should be utilized that are far from each other to be more isolated and decouple interference between the receive power link and the transmit uplink. A treatment system in accordance with embodiments of the invention may adaptively set transmit mode and/or data rates and utilize variable power, rather than target a specific power budget and data rate.

Although specific implantable treatment devices are described above with respect to FIG. 3, one skilled in the art would recognize that certain components of the implantable treatment device described above may be different, may have different characteristics, or be different in number in accordance with embodiments of the invention as appropriate to the requirements of a particular application in accordance with embodiments of the invention.

Figure 4:
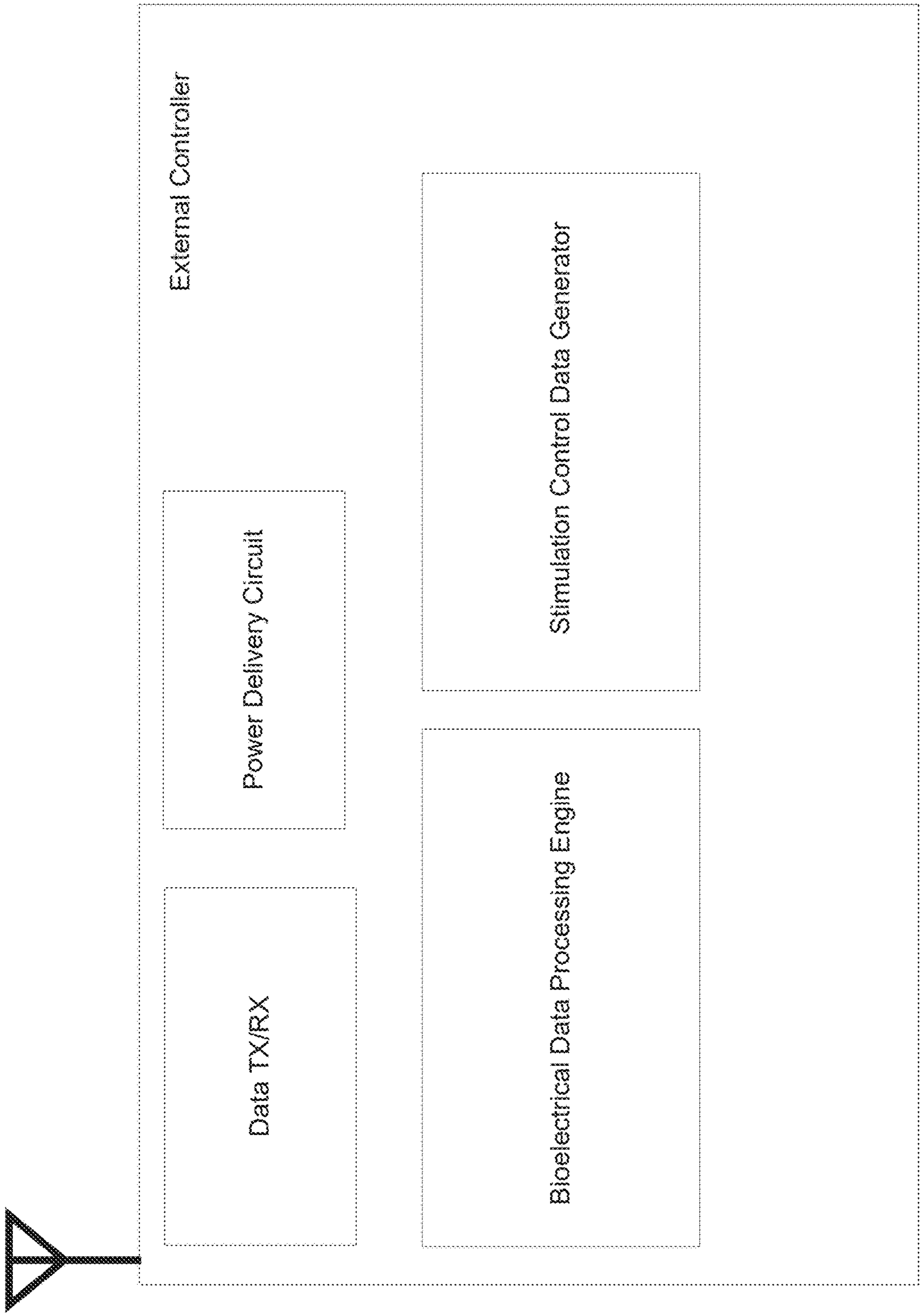
FIG. 4 illustrates a system architecture of an external controller for processing bioelectrical data and generating stimulation control signals to be transmitted to one or more implanted treatment devices in accordance with an embodiment of the invention.

FIG. 4 illustrates a circuit architecture of an external controller in accordance with an embodiment. The external controller can include a data receiver and/or transmitter (TX/RX), a power delivery circuit, a bioelectrical data processing engine, and a stimulation control data generator. The external controller can receive bioelectrical e.g., neural data from one or more implantable treatment devices. The received neural data can be processed. One or more stimulation parameters can be generated based on the processed neural signal data. The data TX/RX can transmit the stimulation control signals to one or more implantable treatment devices in order to perform a stimulation. The power delivery circuit can provide power to one or more implantable treatment devices. In certain embodiments, the power can be delivered wirelessly to the implantable treatment devices. In several embodiments, the power can be delivered through wires to the implantable treatment devices.

Although FIG. 4 illustrates a particular circuit architecture of an external controller, any of a variety of system architectures can be utilized as appropriate to the requirements of a specific application in accordance with embodiments of the invention.

Figure 5A:
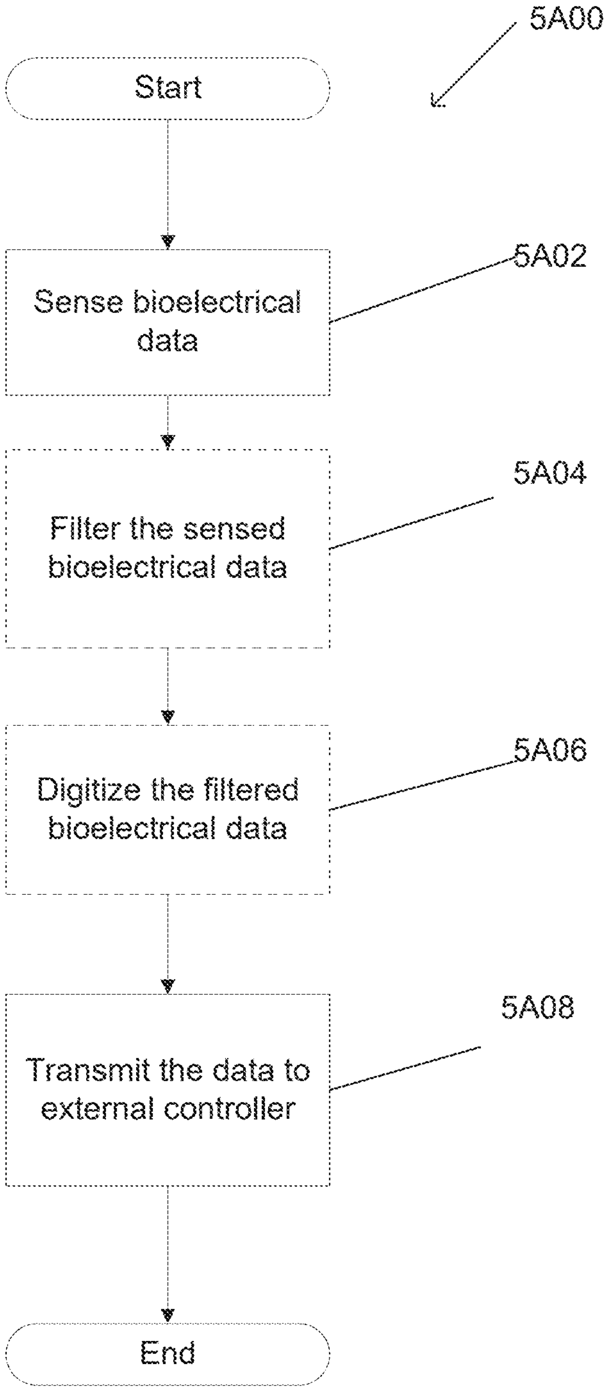
FIG. 5A illustrates a process for recording and transmitting bioelectrical data in an implanted treatment device in accordance with an embodiment of the invention.

A process for sensing/recording neural data by an implantable treatment device and transmitting the data to an external controller in accordance with an embodiment of the invention is illustrated in FIG. 5*a*. The process can sense 5*a*02 and record bioelectrical signals. In certain embodiments, the process can filter 5*a*04 the recorded and/or sensed bioelectrical signal. The process can digitize 5*a*06 the bioelectrical signal into corresponding bioelectrical data. The process transmits 5*a*08 the bioelectrical data to an external controller. Although specific processes for recording and transmitting bioelectrical data are described above, any of a variety of processes may be utilized to record and transmit bioelectrical data as appropriate to the requirements of a specific application in accordance with embodiments of the invention.

Figure 5B:
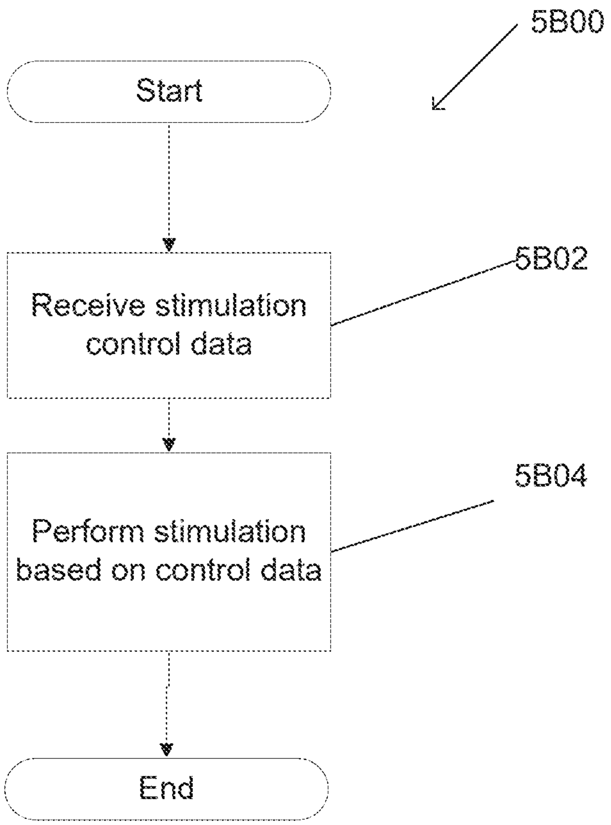
FIG. 5B illustrates a process for receiving and performing stimulation in an implantable treatment device in accordance with an embodiment of the invention.

A process for receiving stimulation control data at an implantable treatment device from an external controller and performing a stimulation in accordance with an embodiment of the invention is illustrated in FIG. 5*b*. The process 5*b*00 receives 5*b*02 stimulation control data from an external controller. In many embodiments, the control data can include one or more different stimulation parameters, including stimulation delivery circuit stimulation pulse duration, amplitude of the stimulation, frequency of the stimulation, and directionality and phase response of the stimulation (mono phasic vs biphasic). The process can perform a stimulation 5*b*04 based on the stimulation control data. The process ends. Although specific processes for performing a stimulation are described above, any of a variety of processes may be utilized perform stimulations as appropriate to the requirements of a specific application in accordance with embodiments of the invention.

Figure 6:
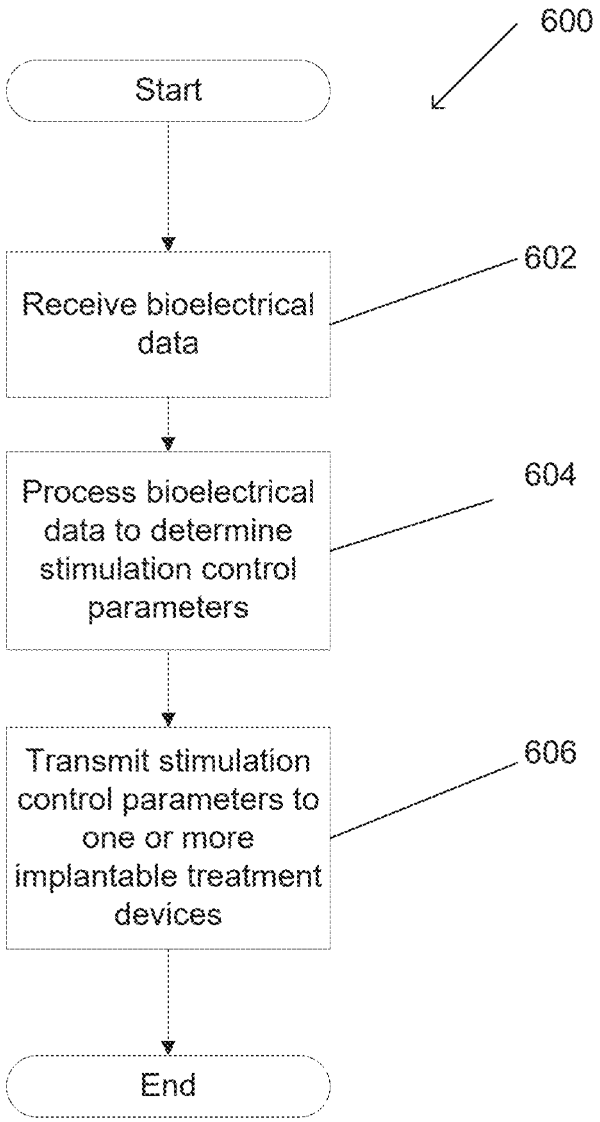
FIG. 6 illustrates a process for processing bioelectrical data within an external controller and transmitting the control signals to an implantable treatment device in accordance with an embodiment of the invention.

A process for generating stimulation control data on an external controller and transmitting the data to one or more implantable treatment devices in accordance with an embodiment of the invention is illustrated in FIG. 6. The process 600 can receive 602 sensed bioelectrical data from one or more implantable treatment devices. The process can process 604 the bioelectrical signal data to determine one or more stimulation control parameters. The process can transmit 606 the stimulation control parameters to one or more implantable treatment devices. The process ends.

In many embodiments, the treatment system can sense bioelectrical signal data after a particular time period after a stimulation has occurred. The time period can be preprogrammed. In several embodiments, the time period can be dynamic based on the measured signal recording and stimulation data.

Figure 7:
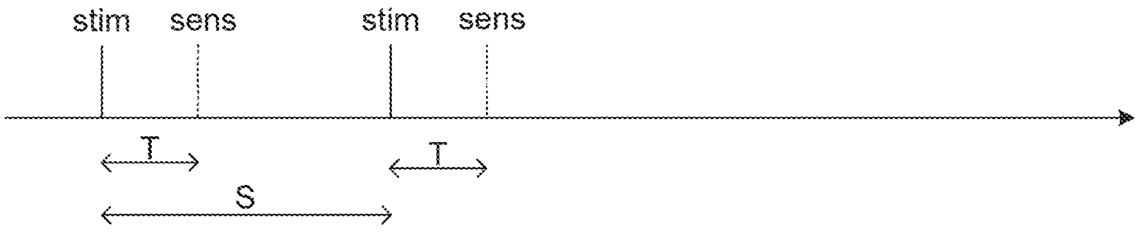
FIG. 7 illustrates a timing diagram for performing stimulation and then sensing and recording bioelectrical data after a particular pre-programmed time period after the stimulation in accordance with an embodiment of the invention.

A timing diagram illustrating sensing bioelectrical data after a time period after stimulation is illustrate in FIG. 7. As illustrated, an external controller can periodically transmit a stimulation control signal to direct an implantable treatment device to deliver a stimulation. In the timeline of FIG. 7, the external controller controls the microchip to deliver stimulation (stim) every S seconds. In certain embodiments, S may be in the range of 1 usec to 100 msec. The stimulation may comprise a single electrical pulse or a train of electrical pulses. The external controller can also send a sense control signal to direct an implantable treatment device to sense (sens) the bioelectrical signals within a preprogrammed time (T) after the stimulation occurs. In certain embodiments, T may be in the range of 1 usec to 100 msec. In many embodiments, this time (T) can be determined by estimating the speed of the transfer of the activated neural signal from the location of the stimulation to the location of the sensing node.

In several embodiments, the preprogrammed time sensing starts at a particular time after a stimulation occurs, where the particular time can be at 1 usec, 10 usec, 100 usec, 1 msec, 10 msec, or 100 msec, among various other set times after the simulation occurs. In certain embodiments, the sensing can be done in an intermittent fashion with a duty cycle of less than a certain percentage. In certain embodiments, the duty cycle can be less than 20%. For example, sensing can be performed for 200 msec every 1 sec. Although a specific timing diagram for performing a sensing after a stimulation occurs is illustrated in FIG. 7, any of a variety of timing specifications can be utilized as appropriate to the requirements of specific applications in accordance with embodiments of the invention.

System Architecture of Implantable Pulse Generator

Figure 8A:
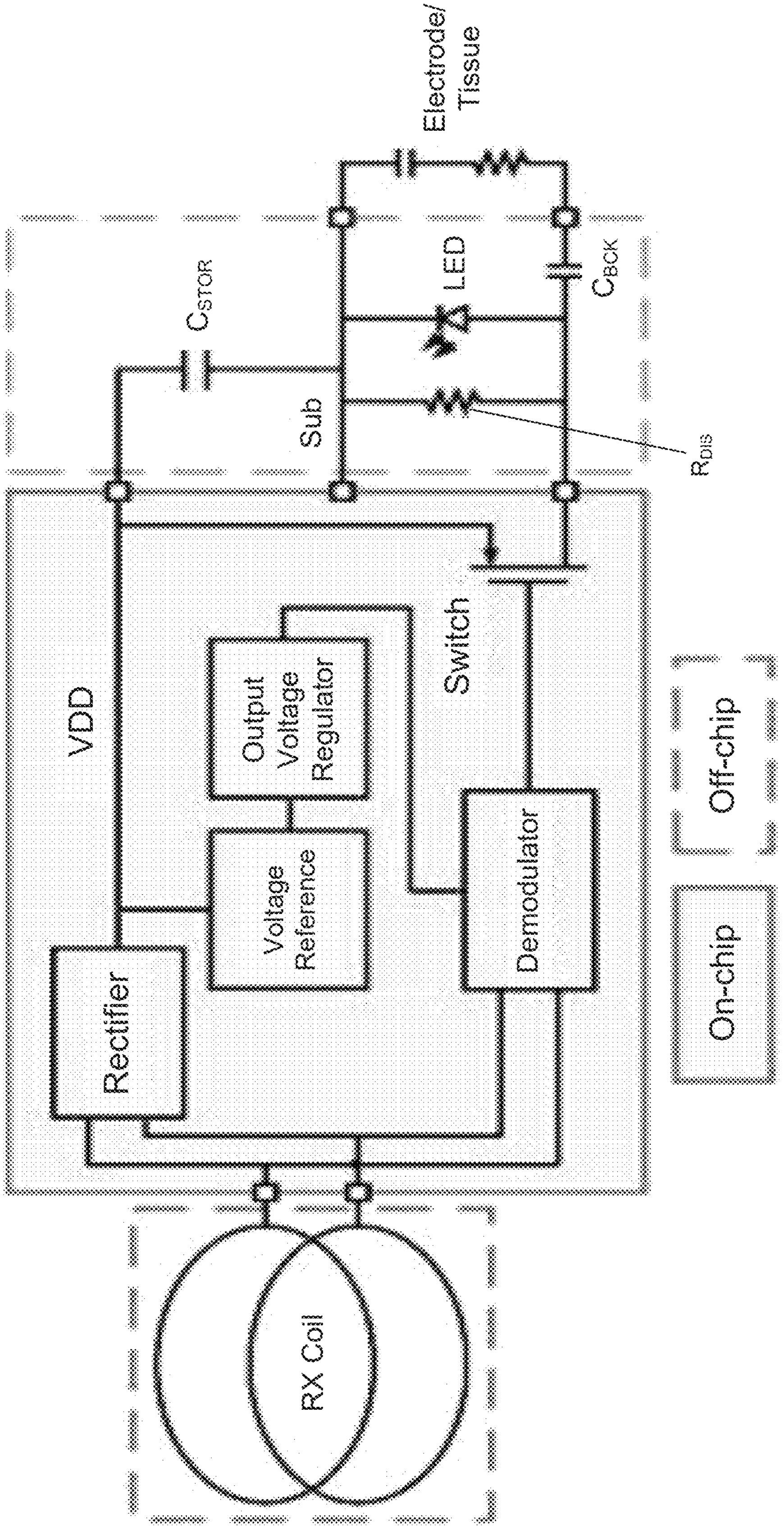
FIG. 8A illustrates a circuitry overview, with the circuit architecture of an implantable treatment device in accordance with an embodiment of the invention.

A system architecture of an implantable treatment device in accordance with an embodiment of the invention is shown in FIG. 8*a*. In many embodiments, the magnetic field coupled to the Rx coil can be rectified to generate VDD and charges an energy storage capacitor, CSTOR. In several embodiments, notches (e.g., RF power is reduced to a percentage of the RF power during harvest) can be intentionally applied in the Tx signal which precisely controls the timing of the output stimulations as their repetitions. The notch-based modulation scheme can eliminate any complex telemetry and minimizes the power consumption. In many embodiments, as the notches only constitute a negligible portion of the Tx power, they do not degrade the efficiency of the power transfer link. In many embodiments, a VCS scheme may be adopted for better energy-efficiency, in which VDD node can be directly applied to the electrode/tissue with a controllable pulse width. In many embodiments, in replacement of a low-dropout (LDO), a simplified output voltage regulator may be used to limit the amplitude of the output stimulations within a specific range, which may further reduce the static power consumption. In many embodiments, the regulator may enable the notch-demodulation block only when the supply voltage exceeds the lower tier. On the contrary, when the supply voltage exceeds the higher tier, a discharge path may be enabled to rapidly discharge the excess incident charge. The stimulations can be delivered through a DC-block capacitor, CBCK, for charge-neutralization. In several embodiments, a discharge resistor, Rois, nulls the accumulated charge on CBCK. A light-emitting diode (LED) can be optionally included at the output. Although FIG. 8*a* illustrates a particular circuit architecture of an implantable treatment device, any of a variety of circuit architectures may be utilized as appropriate to the requirements of specific applications in accordance with embodiments of the invention.

Figure 8B:
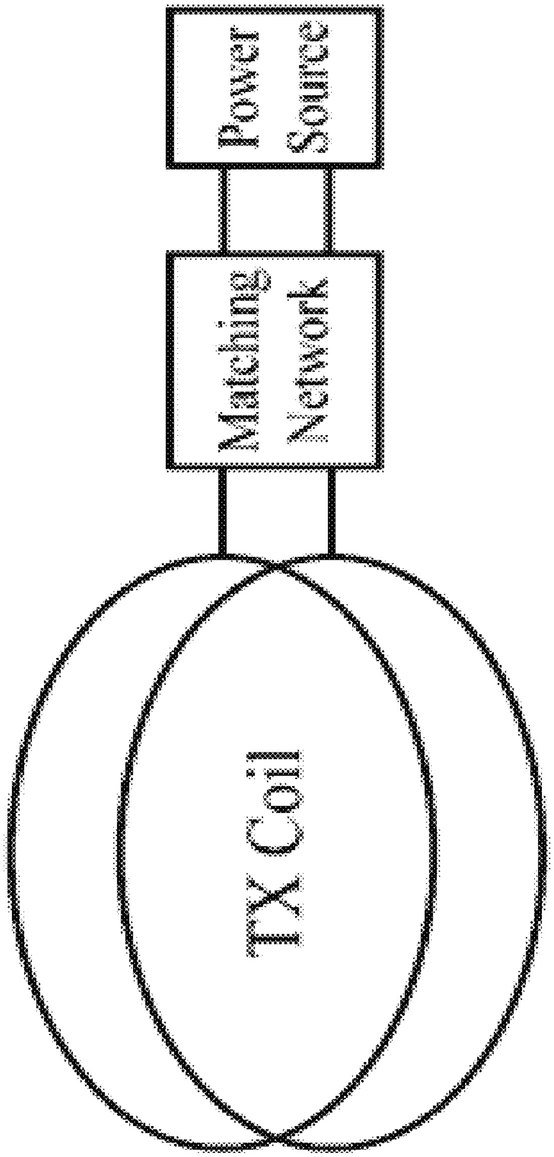
FIG. 8B illustrates a schematic of the Tx coil in accordance with an embodiment of the invention.

In many embodiments, an implantable treatment device can be wirelessly powered and controlled by a custom Tx coil with the diameter of approximately 3 cm, as illustrated in FIG. 8*b* in accordance with an embodiment of the invention. In certain embodiments, a matching network ensures the impedance matching at approximately 430 MHz, the resonant frequency of the Rx energy-harvesting front-tend. Although FIG. 8*b* illustrates a particular schematic of a Tx coil, any of a variety of architectures may be utilized as appropriate to the requirements of specific applications in accordance with embodiments of the invention.

In many embodiments, an implantable treatment device can improve the spatiotemporal resolution of the recorded signals to provide more insight into the complex mechanism of human functions. A higher spatiotemporal resolution necessitates signal recording from a smaller area with a higher recording rate. To enable recording at a fine scale, many embodiments provide implantable system-on-chips (SoCs) to realize a distributed bioelectrical recording system. The system-level requirements of such SoCs in accordance with many embodiments are long-term wireless operation, mm-sized form factor, and integration capability on a commercial CMOS process to make them scalable and cost-efficient. Miniaturizing the size of an implantable treatment device can address the needs of treatment systems since it can result in a higher sensor density and also enables signal recording at an ultra-small structural scale.

Figure 9:
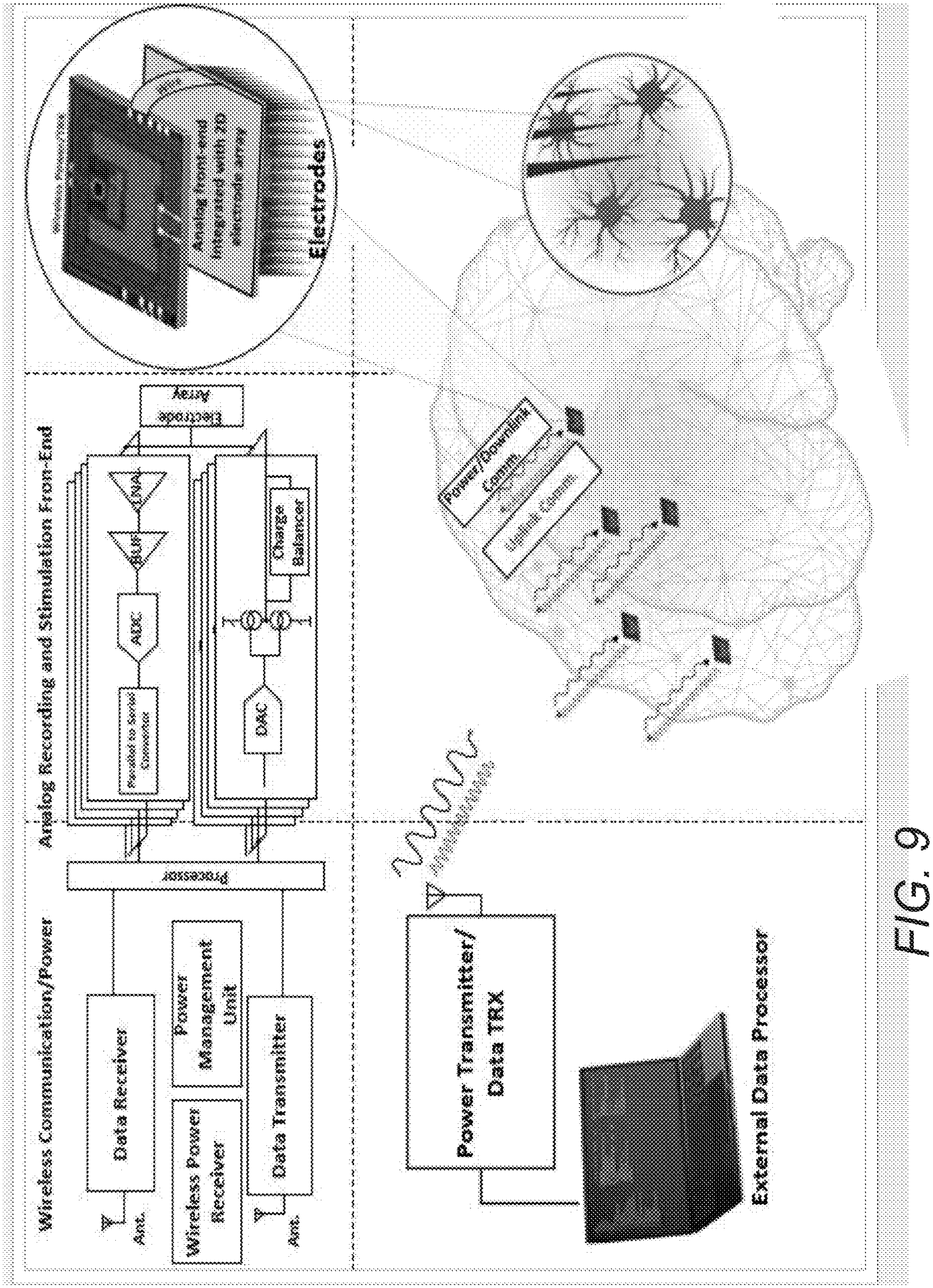
FIG. 9 illustrates a closed-loop treatment system for neural recording and stimulation for neural prostheses in accordance with an embodiment of the invention.

FIG. 9 illustrates a conceptual treatment system with a multi-site and distributed neural interface enabled by multiple mm-sized implantable treatment devices in accordance with an embodiment of the invention. Each implantable treatment device can include a data transceiver (TRX) that is placed on top of a microelectrode array. Because of the compact size, individual implantable treatment devices can be tightly placed on a body part (e.g., the brain) to improve the recording resolution. There are various challenges toward realizing a practical neural interface system. Accordingly, many embodiments of the treatment system address the data communication problem and provide a TRX compatible with the system-level requirements of implantable treatment systems. In many embodiments, each TRX can acts as a communication hub between the electrodes within an implantable treatment device and an external controller. Recent neural recording systems have reported up to 4096 recording electrodes. On the other hand, various recording methods such as ECOG or spike recording demand different sampling rates that may reach as high as 10 ksps per channel. Hence, the overall communication bandwidth may exceed tens of Mbps.

A practical TRX in accordance with many embodiments of the invention should support the demanded bandwidth and be compatible with most all of the system-level requirements of miniaturized implants. Achieving such a high data rate can be difficult due to severe power budget constraints and poor performance of electrically small antennas used for power-harvesting and data communication. Considering the specific absorption-rate (SAR) limit of various biological tissues and nonidealities of a WPT system such as coil misalignment and link variations, the maximum harvested power by mm-sized power harvesters can be about few hundreds of micro-Watts. Moreover, the wavelength of EM waves at the frequencies that data communication is typically conducted ranges from tens to hundreds of centimeters. A mm-sized antenna is often much smaller than the wavelength and has poor radiation efficiency. Accordingly, many embodiments provide for a TRX for mm-sized implantable treatment devices that can achieve a very high-energy efficiency to support high data rates.

Backscattering is a widely adopted technique for telemetry in implantable applications since it results in extremely low-power consumption. The transmitted data pattern can be used for load shift keying (LSK) modulation of the power coil and alters the reflected signal to an external reader. Despite achieving a superior energy efficiency over active communication, backscattering radios fail to address the main requirements of mm-sized implants. Due to the small size of the power coil and a strong power carrier, which acts as a blocker, detection of the reflected signal on the reader side may be difficult or even impossible. In addition, modulating the power coil disrupts the power flow into the system and degrade power-transfer efficiency. Furthermore, the communication bandwidth of backscattering radios is often very low due to the high-quality factor (Q) of the power coil that limits the data rate, consequently.

Active TRXs may not face the challenges of their backscattering counterparts and can potentially achieve high data rates at the expense of higher power consumptions. Considering the stringent power budget in implantable applications, a design goal of many embodiments of the treatment system can be achieving the highest possible energy efficiency; hence, proper modulation schemes can be chosen. There is a trade-off between energy efficiency and spectral efficiency in communication systems. Narrowband modulation schemes demand a relatively complex architecture to generate an accurate frequency whereas wideband modulation schemes such as on-off keying (OOK) have often less complexity and result in higher energy efficiency.

Accordingly, many embodiments provide for the design, implementation, and verification of a fully integrated and RF-powered wireless data TRX. The radio in accordance with many embodiments of the system can achieve state-of-the-art energy efficiency and the smallest form factor compared with prior mm-sized wirelessly powered active radios.

In many embodiments, the implantable treatment device can be implemented on a single CMOS silicon chip and all needed components for power delivery, energy storage, bioelectrical sensing, stimulation, and data communication, including an on-chip coil (OCC) and a dipole antenna, can be implemented on the same chip. The TRX in accordance with many embodiments of the implantable treatment device can be designed to enable simultaneous power delivery and data communication through two distinct wireless links separated in the frequency domain. In many embodiments, the implantable treatment device can support data rates of up to 2.5 Mbps in the RX and data rates of up to 150 Mbps in the TX chain, respectively. In many embodiments, the implantable treatment device can provide for fully on-chip integration that can result in cost reduction, elimination of any post-fabrication process, and reliability improvement among other benefits. Although FIG. 9 a particular system architecture of a closed-loop treatment system with several implantable treatment device for neural recording and stimulation system for neural prostheses, any of a variety of system architectures can be utilized as appropriate to the requirements of specific applications in accordance with embodiments of the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An implantable treatment device, comprising:

an energy harvesting circuit configured to harvest ambient energy and establish a voltage across a storage capacitor, wherein the ambient energy is at least one energy selected from the group consisting of ambient electrical, magnetic energy, and electromagnetic energy;

a sensing circuit coupled to the storage capacitor, the sensing circuit configured to sense bioelectrical signals and generate bioelectrical signal data;

a stimulator circuit coupled to the storage capacitor and a set of electrodes, the stimulator circuit configured to deliver a stimulation via at least one electrode from the set of electrodes based on a set of control signals received from an external controller that determine a set of parameters of the stimulation; and a communication circuit coupled to the storage capacitor, the communication circuit configured to (1) transmit to the external controller the bioelectrical signal data and (2) control the stimulator circuit to deliver energy via at least one electrode from the set of electrodes in response to the control signals received from the external controller, wherein operation of the communication circuit and the sensing circuit are duty-cycled relative to operation of the energy harvesting circuit to maintain a minimum voltage across the storage capacitor.

2. The implantable treatment device of claim 1, wherein the bioelectrical signal is at least one signal selected from the group consisting of a neural signal, a neural LFP (local field potential), an electrocardiogram (ECG) signal, a compound action potential, an electromyogram (EMG) signal, an Electroencephalogram (EEG) signal, an Electromyogram (EMG) signal, an Electrooculogram (EOG) signal, an Electroretinogram (ERG) signal, and an Electrogastrogram EGG) signal.

3. The implantable treatment device of claim 1, wherein the sensing circuit digitizes the bioelectrical signals to generate bioelectrical signal data.

4. The implantable treatment device of claim 1, wherein the bioelectrical signal data are used to optimize a plurality of parameters of the stimulation delivered by the stimulator circuit.

5. The implantable treatment device of claim 4, wherein the plurality of parameters includes at least one parameter selected from the group consisting of the stimulation pulse duration, amplitude of the stimulation, frequency of the stimulation, and directionality and phase response of the stimulation (mono phasic vs biphasic).

6. The implantable treatment device of claim 1, wherein the implantable treatment device is a closed loop neural stimulation system.

7. The implantable treatment device of claim 1, wherein the bioelectrical signals are neural signals that range from 1 uV to 100 mV.

8. The implantable treatment device of claim 1, further comprising filter circuitry that filters the bioelectrical signals and digitizes the filtered bioelectrical signals.

9. The implantable treatment device of claim 8, wherein the filter circuitry is designed to pass signals from 0.1 Hz to 10 KHz.

10. The implantable treatment device of claim 8, wherein the filter circuitry passes more of a frequency content of the bioelectrical signal while removing out of band noise.

11. The implantable treatment device of claim 1, wherein the bioelectrical signals are sensed within a preprogrammed time after a stimulation occurs, wherein the preprogrammed time sensing starts at a particular time after a stimulation occurs, where the particular time is a time selected from the group consisting of 1 usec, 10 usec, 100 usec, 1 msec, 10 msec, and 100 msec after the simulation occurs.

12. The implantable treatment device of claim 11, wherein the preprogrammed time sensing starts at a particular time after a stimulation occurs, where the particular time is a time selected from the group consisting of 1 usec, 10 usec, 100 usec, 1 msec, 10 msec, and 100 msec after the simulation occurs.

13. The implantable treatment device of claim 1, wherein the sensing is done in an intermittent fashion with a duty cycle of less than 20%.

14. The implantable treatment device of claim 1, wherein the control signals provide a plurality of stimulation parameters that are optimized for the stimulation using data from a plurality of different patients.

15. The implantable treatment device of claim 1, wherein the control signals provide a plurality of stimulation parameters that are optimized for the stimulation with respect to a specific patient.

16. The implantable treatment device of claim 1, wherein the external controller processes the bioelectrical signal data to generate the set of control signals.

17. The implantable treatment device of claim 1, wherein the energy harvesting circuit is wirelessly powered.

18. The implantable treatment device of claim 1, wherein the stimulator circuit stimulates a body part in at least one body region selected from the group consisting of peripheral nerves, spinal cord, vagus nerve, central nervous system, sacral nerve, occipital nerve, hypoglossal nerve, kidney, bladder, brain, lung, heart, muscle, and fat.

19. The implantable treatment device of claim 1, wherein the set of control signals provide a plurality of stimulation parameters for the stimulation that are optimized using processing performed in a cloud server.

20. The implantable treatment device of claim 1, wherein the energy harvesting circuit comprises using energy from at least one capacitor.

21. A method of therapy delivery by a treatment system, the method comprising:

harvesting, at at least one implantable treatment device placed at an implant site, ambient energy to establish a voltage across a storage capacitor;

sensing, through the at least one implantable treatment device, bioelectrical activity at the implant site;

transmitting, through the at least one implantable treatment device, bioelectrical data corresponding to sensed bioelectrical activity to an external controller;

receiving, through at least one implantable treatment device placed at an implant site, stimulation control data derived at least in part from the bioelectrical data by the external controller; and delivering, through the at least one implantable treatment device, a stimulation based on the stimulation control data, wherein the sensing, transmitting and delivering are duty cycled relative to the harvesting and the receiving to maintain a minimum voltage across the storage capacitor.

22. The method of claim 21, wherein the at least one implantable treatment device comprises a stimulation set of electrodes spaced apart from a sensing/recording set of electrodes, and the method further comprising:

estimating a time window where a neural signal activated by a stimulation signal delivered by the stimulation set of electrodes arrives at the sensing/recoding set of electrodes;

determining a time based on the estimated time window; and sensing/recording bioelectrical signals via the sensing/recording set of electrodes according to the determined time.

23. The method of claim 21, wherein the at least one implantable treatment device comprises a stimulation set of electrodes spaced apart from a sensing/recording set of electrodes, and the method further comprising:

estimating a speed of travel of an activated neural signal from a location of stimulation set of electrodes to a location of the sensing/recoding set of electrodes;

determining a time based on the estimated speed; and sensing/recording bioelectrical signals via the sensing/recording set of electrodes according to the determined time.

24. The method of claim 21, wherein the at least one implantable treatment device comprises a stimulation set of electrodes spaced apart from a sensing/recording set of electrodes, and the method further comprising:

measuring an evoked compound action potential (ECAP) based on bioelectrical signals sensed at the sensing/recording set of electrodes;

transmitting the measure of ECAP to the external controller; and adjusting one or more stimulation parameters based on the ECAP, to maintain an appropriate level of neural activity.

* * * * *